United States Patent [19]
Reggiardo

[11] Patent Number: 5,694,949
[45] Date of Patent: Dec. 9, 1997

[54] VARIABLE CAPACITANCE EMULATION CIRCUIT FOR ELECTROPHYSIOLOGY DIAGNOSTIC DEVICE

[75] Inventor: Christopher V. Reggiardo, Alviso, Calif.

[73] Assignee: Pacesetter, Inc., Sunnyvale, Calif.

[21] Appl. No.: 692,682

[22] Filed: Aug. 6, 1996

[51] Int. Cl.$^6$ .................................................. A61B 5/00
[52] U.S. Cl. ................................ 128/897; 323/354
[58] Field of Search .......................... 323/298, 297, 323/353, 354, 369; 128/897

[56] References Cited

U.S. PATENT DOCUMENTS 3,624,530  11/1971  Zwim ............................. 323/354

*Primary Examiner*—Scott Getzow
*Attorney, Agent, or Firm*—Steven M. Mitchell

[57] ABSTRACT

An electrophysiology diagnostic device generating a high voltage (HV) pulse of a predetermined shape, which device is electrically connected to a patient's heart, i.e., a load resistance and which device includes a microprocessor and a load resistance measuring device, includes a variable capacitance emulation (VCE) circuit. The VCE circuit, which is capable of emulating a selected capacitance C, includes a fixed capacitor $C_0$, and first and second branch circuits including respective resistors $R_1$ and $R_2$ and corresponding switching elements, connected in parallel with the load resistance $R_L$. According to one aspect of the VCE circuit, the selected capacitance C satisfies the expression $C=[(R_L \| R_{eff})*C_0]/R_L$, where $R_{eff}$ is an effective resistance value produced by pulse width modulation control of at least one of the resistors $R_1$ and $R_2$ using corresponding switch elements. A method for operating a branch network to emulate a predetermined resistance is also described.

19 Claims, 14 Drawing Sheets

| ID | RANGE | R1 ON | R1 OFF | MAX ERROR (%) | ENCODING |
|---|---|---|---|---|---|
| 1 | R2 \|\| [R3] \|\| R4 | 5.74 - 6.91 | 11.0 - 16.3 | 0.66 at 13.1Ω | "xx 11 10 11" |
| 2 | [R2] \|\| R3 \|\| R4 | 5.78 - 7.52 | 11.1 - 20.1 | 1.74 at 14.3Ω | "xx 10 11 11" |
| 3 | R2 \|\| [R3 & R4] | 5.97 - 6.95 | 11.9 - 16.5 | 0.53 at 13.8Ω | "xx 11 10 01" |
| 4 | R2 \|\| [R3] | 6.00 - 7.30 | 12.0 - 18.6 | 0.67 at 14.6Ω | "xx 11 10 00" |
| 5 | [R2] \|\| R3 | 6.05 - 7.98 | 12.2 - 23.8 | 1.75 at 16.1Ω | "xx 10 11 00" |
| 6 | [R2 & R3] \|\| R4 | 7.16 - 7.73 | 17.7 - 21.7 | 0.46 at 19.5Ω | "xx 10 01 11" |
| 7 | [R2 & (R3 \|\| R4)] | 7.53 - 7.78 | 20.2 - 22.1 | 0.19 at 21.1Ω | "xx 10 01 01" |
| 8 | [R2 & R3] | 7.57 - 8.22 | 20.5 - 26.1 | 0.46 at 23.0Ω | "xx 10 01 00" |
| 9 | [R4] \|\| R3 | 7.86 - 8.25 | 22.7 - 26.5 | 0.14 at 24.5Ω | "xx 00 11 10" |
| 10 | [R3] \|\| R4 | 8.04 - 10.56 | 24.4 - 87.8 | 0.68 at 38.2Ω | "xx 00 10 11" |
| 11 | [R3 & R4] | 8.52 - 10.64 | 29.3 - 94.1 | 0.54 at 44.7Ω | "xx 00 10 01" |
| 12 | [R3] | 8.57 - 11.49 | 30.0 - 270.0 | 0.68 at 54.0Ω | "xx 00 10 00" |
| 13 | [R4] | 11.08 - 11.89 | 144.4 - 1300 | 0.14 at 260.0Ω | "xx 00 00 10" |

| $R_L$ | For $C_0 = 135$ μf and $C = 100$ μf ||| For $C_0 = 180$ μf and $C = 100$ μf |||
|---|---|---|---|---|---|---|
| | $R_{EFF}$ | α1 | PWM Type | $R_{EFF}$ | α1 | % Error | PWM Type |

| $R_L$ | $R_{EFF}$ | α1 | % Error | PWM Type | ... | $R_{EFF}$ | α1 | % Error | PWM Type |
|---|---|---|---|---|---|---|---|---|---|
| 15  | 42.9  | .53 | 0.53 | 11: [R3 & R4] | ... | 18.8  | .66 | 0.31 | 6: [R2 & R3] ∥ R4 |
| 20  | 57.1  | .33 | 0.48 | 11: [R3 & R4] | ... | 25.0  | .39 | 0.10 | 9: [R4] ∥ R3 |
| 25  | 71.4  | .21 | 0.37 | 11: [R3 & R4] | ... | 31.3  | .83 | 0.23 | 11: [R3 & R4] |
| 30  | 85.7  | .14 | 0.25 | 11: [R3 & R4] | ... | 37.5  | .65 | 0.37 | 11: [R3 & R4] |
| 35  | 100.0 | .27 | 0.54 | 12: [R3]      | ... | 43.8  | .52 | 0.40 | 11: [R3 & R4] |
| 40  | 114.3 | .24 | 0.49 | 12: [R3]      | ... | 50.0  | .42 | 0.39 | 11: [R3 & R4] |
| 45  | 128.6 | .21 | 0.45 | 12: [R3]      | ... | 56.3  | .34 | 0.37 | 11: [R3 & R4] |
| 50  | 142.9 | .19 | 0.42 | 12: [R3]      | ... | 62.5  | .28 | 0.33 | 11: [R3 & R4] |
| 55  | 157.1 | .83 | 0.08 | 13: [R4]      | ... | 68.8  | .23 | 0.29 | 11: [R3 & R4] |
| 60  | 171.4 | .76 | 0.10 | 13: [R4]      | ... | 75.0  | .19 | 0.25 | 11: [R3 & R4] |
| 65  | 185.7 | .70 | 0.12 | 13: [R4]      | ... | 81.3  | .16 | 0.22 | 11: [R3 & R4] |
| 70  | 200.0 | .65 | 0.13 | 13: [R4]      | ... | 87.5  | .13 | 0.18 | 11: [R3 & R4] |
| 75  | 214.3 | .61 | 0.14 | 13: [R4]      | ... | 93.8  | .10 | 0.15 | 11: [R3 & R4] |
| 80  | 228.6 | .57 | 0.14 | 13: [R4]      | ... | 100.0 | .27 | 0.40 | 12: [R3] |
| 85  | 242.9 | .54 | 0.14 | 13: [R4]      | ... | 106.3 | .25 | 0.39 | 12: [R3] |
| 90  | 257.1 | .51 | 0.14 | 13: [R4]      | ... | 112.5 | .24 | 0.37 | 12: [R3] |
| 95  | 271.4 | .48 | 0.14 | 13: [R4]      | ... | 118.8 | .23 | 0.36 | 12: [R3] |
| 100 | 285.7 | .45 | 0.14 | 13: [R4]      | ... | 125.0 | .22 | 0.35 | 12: [R3] |
| 105 | 300.0 | .43 | 0.14 | 13: [R4]      | ... | 131.3 | .21 | 0.34 | 12: [R3] |
| 110 | 314.3 | .41 | 0.14 | 13: [R4]      | ... | 137.5 | .20 | 0.32 | 12: [R3] |
| 115 | 328.6 | .40 | 0.14 | 13: [R4]      | ... | 143.8 | .19 | 0.31 | 12: [R3] |
| 120 | 342.9 | .38 | 0.13 | 13: [R4]      | ... | 150.0 | .87 | 0.05 | 13: [R4] |

VARIABLE CAPACITANCE EMULATION CIRCUIT FOR ELECTROPHYSIOLOGY DIAGNOSTIC DEVICE

BACKGROUND OF THE INVENTION

The present invention relates generally to an electrophysiology diagnostic device employed during the implantation of an implantable cardioverter-defibrillator (ICD). More specifically, the present invention relates to an electrophysiology diagnostic device including a variable capacitance emulation circuit.

A healthy heart beats approximately 100,000 times a day and pumps about five quarts of blood each minute. The heart beat is regulated by electrical impulses or signals, which signals originate in the heart's natural pacemaker, the sinoatrial (SA) node. The SA node, which is located in the right atrium, produces very small electrical impulses that vary in rate depending upon the body's demands for oxygen and nutrients. Typically, the SA node controls the heart rate in the range of 60 to 80 heart beats per minute (bpm) in an average person at rest. These signals first cause the atria to contract and are then routed to the ventricles, causing the latter to contract, via the atrioventricular (AV) Node.

If the heart's own electrical signal is interrupted, delayed, or stopped, heart rhythm disturbances, i.e., arrhythmia, can result. Cardiac arrhythmia is classified as either bradyarrhythmia or tachyarrhythmia. In bradyarrhythmia or bradycardia, the heart rate is too slow to meet the body's demands; in tachyarrhythmia, the heart rate is fast but inefficient so that the heart cannot meet the body's blood circulation demands. Tachyarrhythmia is further subdivided into tachycardia and fibrillation. Tachycardia generally signifies a resting heart rate in excess of 100 bpm while fibrillation signifies a heart beat which is so fast and random that blood circulation, for all practical purposes, stops. Tachyarrhythmia, particularly ventricual fibrillation, is a life threatening condition.

A recently introduced medical device, the implantable cardioverter-defibrillator (ICD), delivers bradycardia pacing and tiered therapy, i.e., three different therapeutic electrical impulses to the heart: antitachycardia pacing; cardioversion; and defibrillation. ICDs are electrical devices, about the size of a deck of cards, that are attached to one or more leads or wires inside or outside of the heart, and are implanted into either the patient's chest or abdomen. These devices can detect and treat very fast, lethal heart rhythms by either shocking the heart or pacing the heart back to a normal rhythm. Most ICD's utilize diagnostic algorithms base primarily on sensed heart rate to identify tachyarrhythmias. For example, a device may be programmed to identify tachyarrhythmia for a sensed heart rate of 180 bpm or greater. If it senses that the average heart rate for a predetermined number of intervals is greater than or equal to 180 bpm, it will initiate either anti-tachycardiac pacing or a high voltage (HV) cardioversion pulse according to its programmed parameters. Many ICDs also offer electrogram (EGM) storage of arrhythmia events treated by the ICD.

ICD implantation requires a surgical procedure which has evolved over time. The most common technique currently used includes a non-thoracotomy, lead alone approach which involves insertion of one or more transvenous leads into the subclavian vein in the shoulder after which the lead is advanced into the right ventricle of the heart. The proximal end of the lead is attached to the ICD placed in the chest (like a pacemaker). If needed, a small subcutaneous patch electrode may be implanted under the skin on the left lateral chest wall.

The output stage 100 of a typical ICD is illustrated schematically in FIG. 1. The illustrated resistance-capacitance (RC) circuit consists of a capacitor $C_0$ for supplying a controlled electrical HV pulse to the load resistance $R_L$, i.e., the patient's heart and the leads connected thereto, via a switch assembly $S_0$, which is shown as a double pole, double throw (DPDT) type switch assembly. It will be appreciated that the electrical pulse delivered to the load $R_L$ exhibits a high voltage peak soon after switch assembly $S_0$ is closed, followed by exponential decay of the voltage through load resistance $R_L$. Many advanced ICDs apply a so-called biphasic pulse to load resistance $R_L$, as shown in FIG. 2, by reversing the leads running to the load resistance $R_L$ during the pulse period. It will be appreciated that $V_{1i}$ and $V_{1f}$ and that $V_{2i}$ and $V_{2f}$ in FIG. 2 refer to the initial and final voltages of pulses $P_1$ and $P_2$, respectively, of pulse widths $PW_1$ and $PW_2$. The specified pulse shape can also be derived by switching between two capacitors located in the ICD, as discussed below. Hereinafter, the delivered, exponentially decaying HV electrical pulse shall be referred to using the generic term "HV pulse" irrespective of the output waveform.

It will also be appreciated that the energy E stored by the capacitor $C_0$ is given by the expression:

$$E = 0.5 * C_0 * V^2 \quad (1)$$

where E is the energy in joules, $C_0$ is the capacitance in farads (F) and V is the voltage in volts. Pacing pulses (delivered from a separate, independent output stage) are normally in the range of micro- to millijoules; cardioversion pulses generally range between 1.0 and 5.0 joules. Defibrillation therapy applies HV pulses delivering from 5.0 to 50 joules to the patient's heart per pulse.

During implantation of the ICD device, two parameters are typically determined. First, the load resistance $R_L$, i.e., heart impedance and lead resistance, is determined. Load resistance $R_L$ must be assumed to be an unknown at first since it is a complicated function of a given patient's heart and the ICD lead placement. Moreover, since it should be assumed that the patient impedance may vary somewhat from shock to shock due to possible repositioning of the leads, i.e., changes in the electrode/tissue interface, patient safety considerations suggest that a determination of $R_L$ should be made via a measurement at the beginning of or immediately following each HV pulse event. For example, the electrophysiology apparatus described in commonly assigned U.S. Pat. Nos. 5,115,807, 5,014,697 and 4,827,936, which patents are incorporated herein by reference for all purposes, disclose that the load resistance $R_L$ is not determined until the HV pulse event has been completed. Since the amount of energy delivered to a patient and the rate of change in the HV pulse energy are greatest during the first portion of the HV pulse exponential decay, the patient impedance should be determined as soon as possible in order to limit energy delivery to the patient's heart in excess of that needed for defibrillation. Conventional measurement systems in such electrophysiology apparatuses permit as much as a 25 Volt error between the desired HV pulse and the actual HV pulse before corrective measures to limit the energy applied to the heart are initiated.

Although the size of the capacitor $C_0$ in the ICD output stage 100 is known, new ICD models are being released every year and they may have different capacitor values. It will be appreciated that the size of the capacitor $C_0$ will impact the useful life of the power supply incorporated into the ICD, i.e., the smaller the capacitor, the longer the power supply will last. However, the smaller the capacitor, the less energy it can deliver and, consequently, the less safety margin it can provide. For that reason, a number of ICD devices, each with a different capacitance, may be provided to the physician for selection during the implantation procedure with the optimum device being selected based on measured defibrillation thresholds (DFTs). Since the electrophysiology diagnostic device should provide at least a corresponding number of exponentially decaying HV pulse waveforms for accurate DFT testing, it is generally accepted that the electrophysiology diagnostic device will contain either a variable capacitor or a selection of fixed capacitors corresponding in size to the capacitors in the available ICD device models, which fixed capacitors can be installed in the electrophysiology diagnostic device one at a time. However, since variable capacitors are generally not available in the 50–150 microfarad ($\mu F$) range, particularly with the compact footprint and low equivalent series resistance (ESR) needed for the electrophysiology diagnostic device, the conventional solution is to use replaceable, interchangeable capacitors. It will also be appreciated that since the capacitors used in ICD devices are fast discharge capacitors, e.g., photoflash capacitors, the cost for providing several interchangeable capacitors for use in the electrophysiology diagnostic device may be prohibitively expensive due to the custom nature of the capacitors, based on the limited number of sizes of suitable, commercially available capacitors.

SUMMARY OF THE INVENTION

The principal purpose of the present invention is to overcome the problems and deficiencies noted in the discussion of related art immediately above.

A primary advantage of the present invention is the emulation of a plurality of exponentially decaying HV pulses with minimal ripple using a fixed capacitor. According to one aspect of the present invention, a bank of circuit branches, each branch containing a fixed resistor and a switching element, is connected in parallel with the load resistance in an RC circuit wherein selected ones of the switching elements are energized so as to simulate a desired effective parallel resistance, permitting adjustment of the RC time constant $\tau$ and thereby permitting emulation of a desired capacitance value.

An object according to the present invention is to provide circuitry emulating a variable capacitance for an exponentially decaying RC waveform using a plurality of Pulse Width Modulated (PWM) controlled resistors.

Another object according to the present invention is to provide a wide dynamic range of emulation of a variable capacitance for an exponentially decaying RC waveform using multiple, parallel PWM controlled resistors.

A still further object according to the present invention is to provide capacitor emulation circuitry permitting simultaneous modulation of multiple PWM controlled resistors ("taps") to reduce waveform ripple (noise).

Yet another object according to the present invention is to provide capacitor emulation circuitry permitting simultaneous modulation of multiple PWM controlled resistors to thereby reduce waveform ripple while maintaining a low part count.

Another object according to the present invention is to provide an operating method for circuitry including multiple PWM controlled resistors whereby the ripple at any operating point for the circuitry is minimized.

These and other objects, features and advantages according to the present invention are provided by a circuit for emulating a variable resistor. Preferably, the circuit includes first and second parallel branches having first and second resistors $R_1$ and $R_2$ and first and second switching elements, respectively. According to one aspect of the invention, an effective resistance ($R_{eff}$) to be emulated by the circuit using the first and second resistors $R_1$ and $R_2$ satisfies the conditions that $R_1 \leq R_{eff} \leq R_2$, and that $R_{eff}=(R_1*R_2)/((\alpha_2*R_1)+(\alpha_1*R_2))$, where $\alpha_1$ and $\alpha_2$ denote respective percentages of a unit time period T during which the first and second switching elements are conducting such that $\alpha_1+\alpha_2=1$ T.

These and other objects, features and advantages according to the present invention are provided by a method for emulating an exponentially decaying waveform associated with a desired capacitance C in a resistor-capacitor (RC) circuit including a capacitor $C_0$ having a fixed capacitance different from the desired capacitance C, the RC circuit including a load resistance $R_L$, the capacitor $C_0$ and parallel first and second branches including first and second resistors $R_1$ and $R_2$ and first and second switching elements, respectively. The method includes steps for determining an effective resistance $R_{eff}$ which, when operated in parallel with the resistance $R_L$ and the actual capacitor $C_0$, produces a decay constant $\tau$ identical to that produced using only the capacitance C and the resistor $R_L$, and, when the capacitor $C_0$ is discharged, operating the first and second switching elements according to the expression $R_{eff}=(R_1*R_2)/((\alpha_2*R_1)+((\alpha_1*R_2))$, where $\alpha_1$ and $\alpha_2$ denote respective percentages of a unit period of time T during which the first and second switching elements are conducting such that $\alpha_1+\alpha_2=1$ T so as to simulate the effective resistance $R_{eff}$ and thereby generate the desired exponentially decaying waveform.

These and other objects, features and advantages according to the present invention are provided by an emulation circuit for emulating a variable resistor. Preferably, the emulation circuit includes a first through fourth parallel branches each containing a resistor $R_N$ and a switching element $S_N$, respectively, and a driver circuit, operatively connected to the respective switching elements $S_N$, for generating at least one pulse width modulation control signal, wherein at least one of the switching elements $S_N$ is turned On and Off responsive to the at least one PWM control signal corresponding to a duty cycle of a corresponding one of the $R_N$ resistors in a range of about 10% to 90%.

These and other objects, features and advantages of the invention are disclosed in or will be apparent from the following description of preferred embodiments.

BRIEF DESCRIPTION OF THE DRAWINGS

The preferred embodiments are described with reference to the drawings in which like elements are denoted by like or similar numbers and in which:

FIG. 12 is a table illustrating dynamic range variation depending on the operating configuration of the resistor taps illustrated in FIG. 9; and FIG. 13 is a table which is useful in understanding the selection of digital words which can be stored in LUT 440 of FIG. 9, in an exemplary case.

DETAILED DESCRIPTION OF THE PREFERRED EMBODIMENTS

Figure 1:
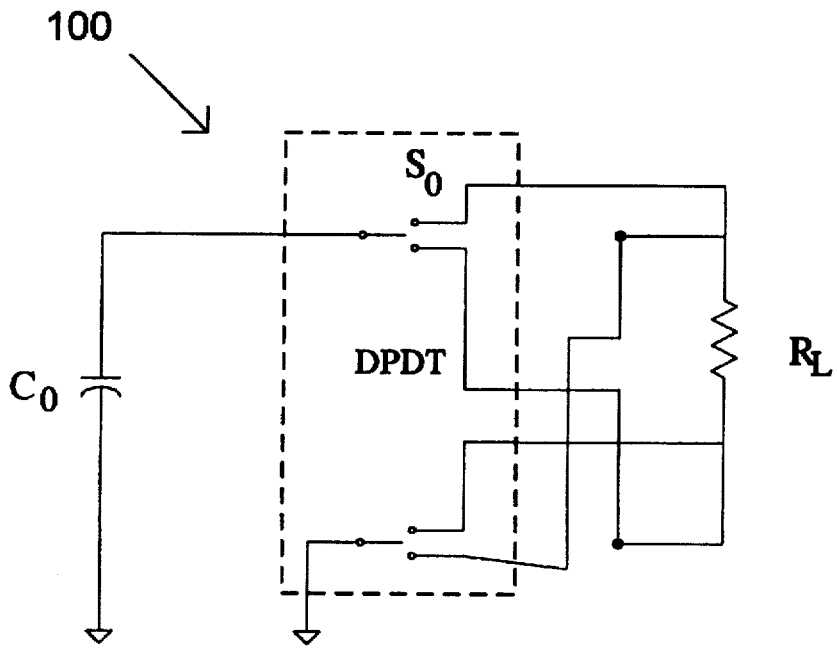
FIG. 1 is a schematic circuit diagram which is useful in understanding the function and operation of an ICD device.
Figure 2:
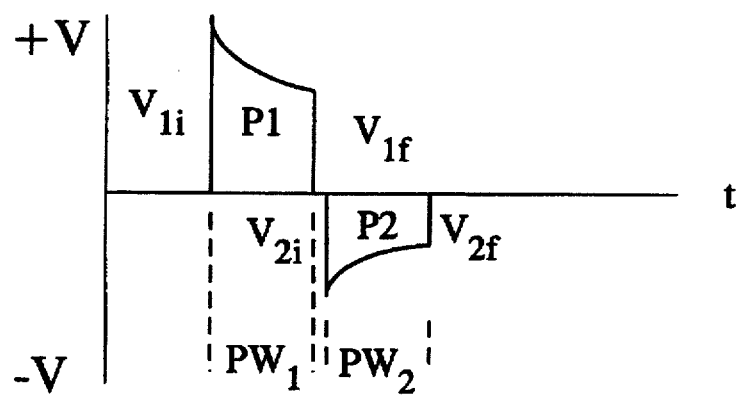
FIG. 2 illustrates a typical biphasic HV pulse produced by the ICD device output stage pictured in FIG. 1.

A preferred embodiment according to the present invention will now be described while referring to FIG. 3, wherein an electrophysiology diagnostic device 200 includes a microcontroller unit (MCU) 500 controlling both a variable capacitance emulation circuit (VCE) 300 and a rapid response voltage threshold determination (RRVTD) circuit 400. According to one aspect of the invention, a plurality of pulse width modulation controlled (PWM controlled) resistor is connected in parallel with the load resistance, in this case a human heart, to emulate a desired resistance-capacitance time constant $\tau$ and thereby model a desired exponentially decaying pulse dissipated by the load resistance. This is the principal function of VCE 300. According to another aspect of the invention, the RRVTD circuit permits early recognition of errors during measurement of an unknown load resistance, thus controlling, e.g., dissipating the excess energy within, the applied voltage pulse in advance of the completion of the actual load resistance measurement. Digital and analog versions of the RRVTD circuit are described below.

Preferably, the RRVTD circuit 400, which is connected to a voltage divider made up of the load resistance $R_L$ and a shunt resistor $R_S$, compares the voltage drop at the shunt resistance $R_S$ with the ideal voltage drop at a given moment in time and generates signals indicative of a voltage mismatch. These signals are received by MCU 500, which advantageously includes an input/output (I/O) circuit 510, a microprocessor 520, a read only memory (ROM) 540 storing operational instructions and a random access memory (RAM) 530 storing refreshable data. The VCE circuit 300 advantageously produces the required HV pulse applied to the load resistance $R_L$ under the control of MCU 500 responsive to the output of RRVTD circuit 400, as will be discussed in greater detail below.

The VCE circuit 300 advantageously emulates a variable capacitance producing an exponentially decaying RC waveform for a given resistive (patient) load $R_L$. Before describing the actual circuit components making up the VCE circuit 300, a brief description of the circuitry's operating principles will first be provided.

Figure 3:
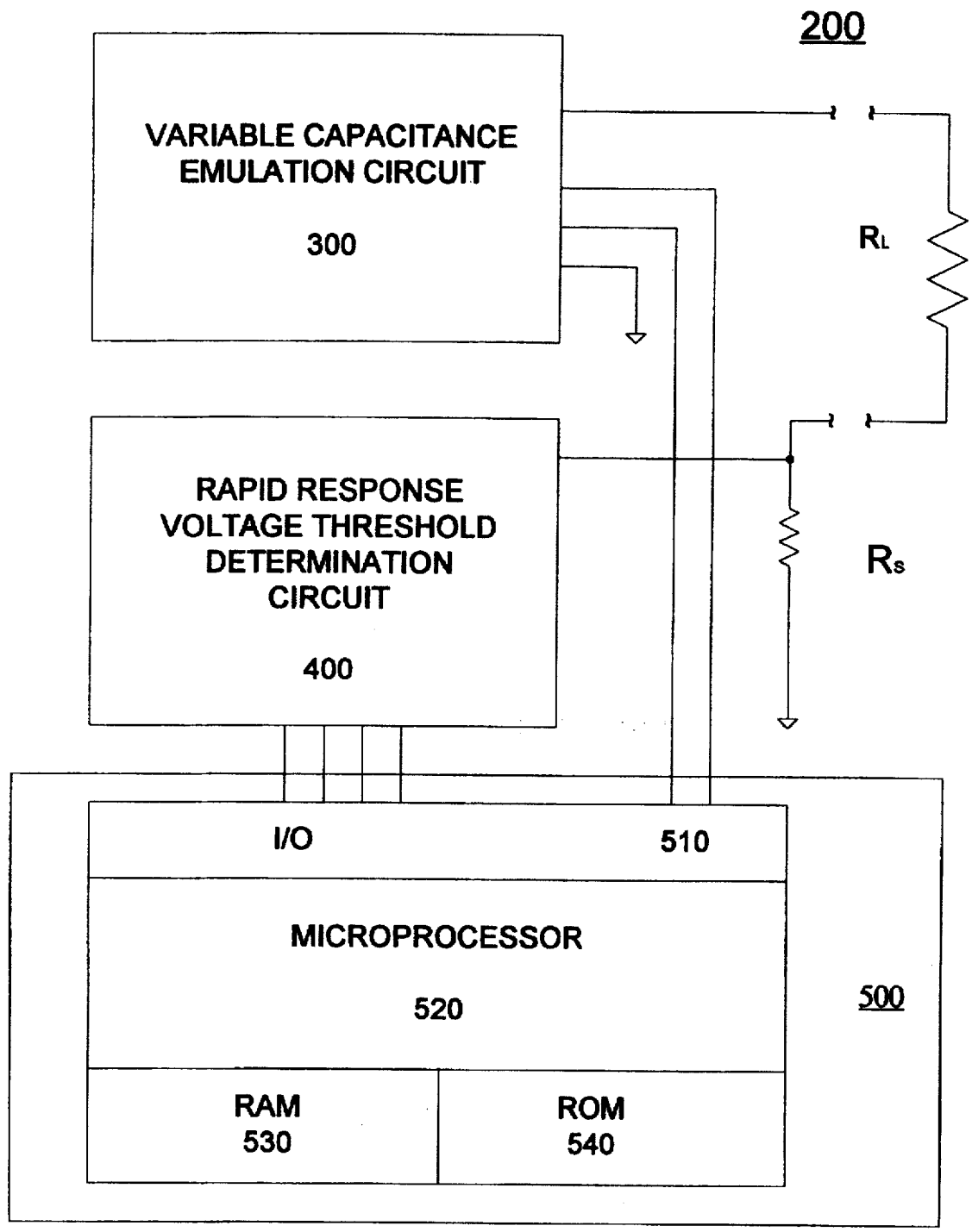
FIG. 3 is a high level, partially block and partially schematic diagram of selected components of an electrophysiology diagnostic device according to the present invention including both a variable capacitance emulation circuit and a rapid response voltage threshold determination circuit.

One of the principal objects of the present invention was the desire to derive an operating method whereby a variable capacitance C could be electronically emulated and used in generating an exponentially decaying RC waveform, i.e., the HV pulse waveform produced by the ICD output stage 100. The emulation of a given capacitance C requires that the time constant Tau ($\tau$) be maintained for a given load resistance $R_L$ where $\tau$ equals the product of a resistance and capacitance, i.e., $\tau=R_i*C_j$, where i and j signify one in a number of possible solutions. Stated another way, for a desired $\tau$, there are any number of capacitance—resistance combinations which will satisfy the constraint imposed by a fixed $\tau$. Thus, as seen from the perspective of load resistance $R_L$, $$\tau = R_L * C \qquad (2)$$

where C is the desired capacitance. When the actual capacitance is $C_0$, it is required that the expression, $$\tau = R_L * C = (R_L \| R_{\mathit{eff}}) * C_0 \qquad (3)$$

where the shunt resistance $R_S$ shown in FIG. 3 is considered negligible, be satisfied. Since $C_0$ is known, nominally by design and accurately through calibration, and C is selected, once load resistance $R_L$ is known, the only remaining unknown, $R_{\mathit{eff}}$, advantageously can be determined from the expression $$R_{\mathit{eff}} = R_L / ((C_0/C) - 1). \qquad (4)$$

As discussed above, the load resistance $R_L$ is first assumed to be an unknown since it is a complicated function of heart physiology and ICD lead placements. $R_L$ is measured using the shunt resistor $R_S$ shown in FIG. 3 according to a method which is discussed in greater detail below. Empirically, the effect of resistor $R_{\mathit{eff}}$ can be seen as siphoning off the excess energy (or current) from $C_0$ so that load resistance $R_L$ sees only the energy (or current) that it would see if a capacitor C of the desired smaller value were provided in place of the actual capacitor $C_0$ in VCE circuit 300.

It should be noted that load resistance $R_L$ will generally fall within the range of 15–120 $\Omega$ and will nominally fall within the range of 20–50 $\Omega$. It should also be noted that the possible range of desired capacitance values for capacitor C is 50 $\mu$F for newer ICD devices through 150 $\mu$F for the current generation of ICDs. From these two design constraints, it was determined that resistor $R_{\mathit{eff}}$ would have to be adjustable over the range of about 6 to 1000 $\Omega$. Although this resistance range could be accommodated by, e.g., a conventional high power decade resistance circuit, the real estate taken up by such a circuit would be a high percentage of the available area for all circuits. Moreover, with conventional decade resistance circuits or even infinitely variable resistors, automatic control of the overall resistance value for resistor $R_{\mathit{eff}}$ sufficient to permit, for example, the emulation of a capacitor C with a non-linear voltage-capacitance characteristic would not be possible.

To accommodate these additional design constraints, it has been discovered that one can use a resistor $R_1$ to produce or simulate $R_{\mathit{eff}}$, where $R_1$ is connected in parallel with load resistance $R_L$ and connected to ground via an electronic switching device $S_1$. See FIG. 4. Advantageously, the switching device $S_1$ can be driven by a pulse width modulation (PWM) driver circuit 320 so that the resistor $R_1$ may be a PWM controlled resistor $R_1$. It will be appreciated from FIG. 4 that resistor $R_1$ is also placed in parallel with the actual capacitor ($C_0$). It should be noted that a PWM controlled resistor $R_1$ exhibits an effective resistance $R_{eff}$ according to the following equation:

$$R_{eff} = R_1/\alpha \quad (5)$$

where $\alpha$ denotes the service factor, i.e., the percentage of time that $R_1$ is connected to ground via switching device $S_1$.

Figure 5:
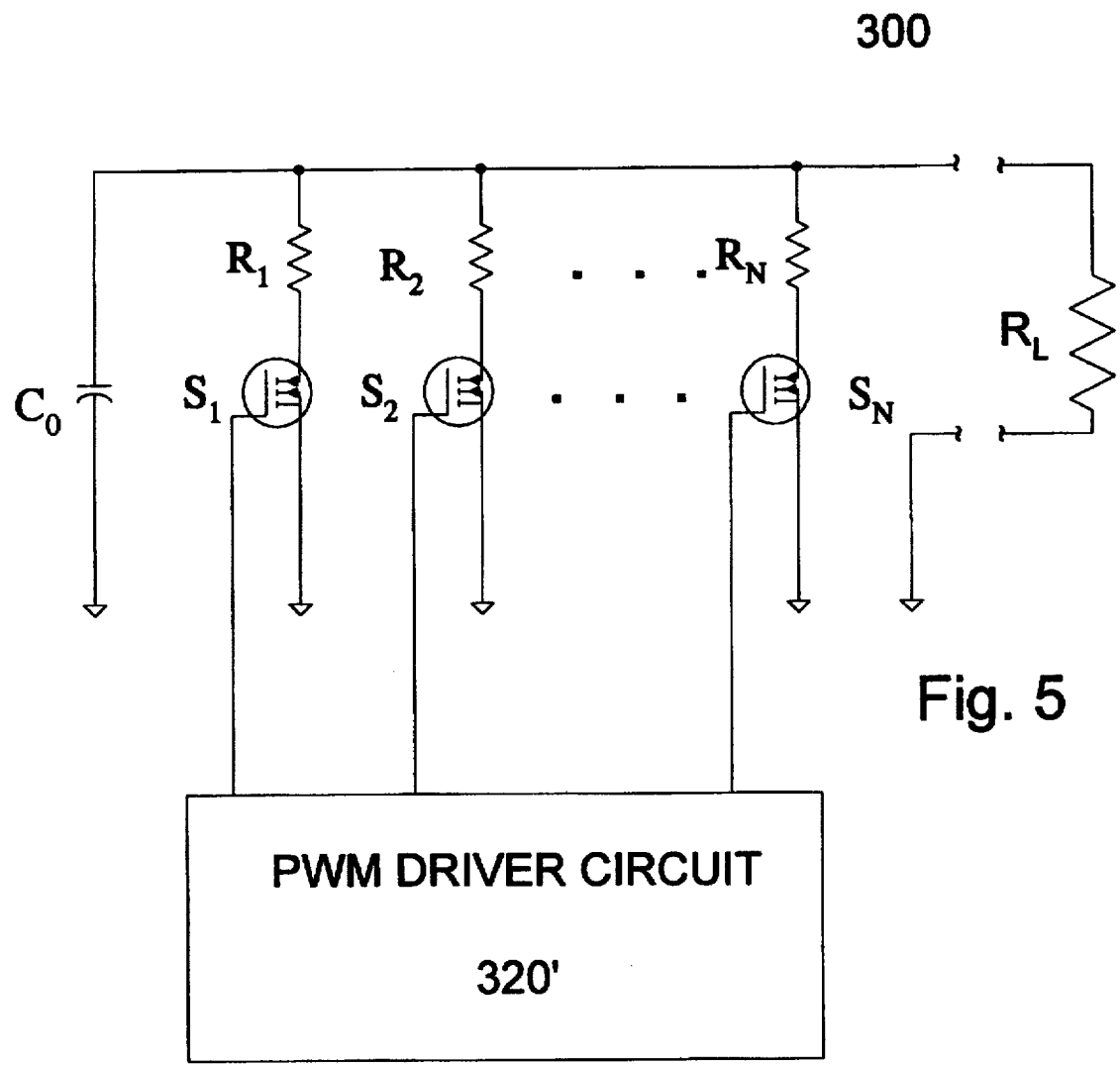
FIG. 5 is a more detailed schematic diagram of the exemplary circuit illustrated in FIG. 4.
Figure 9:
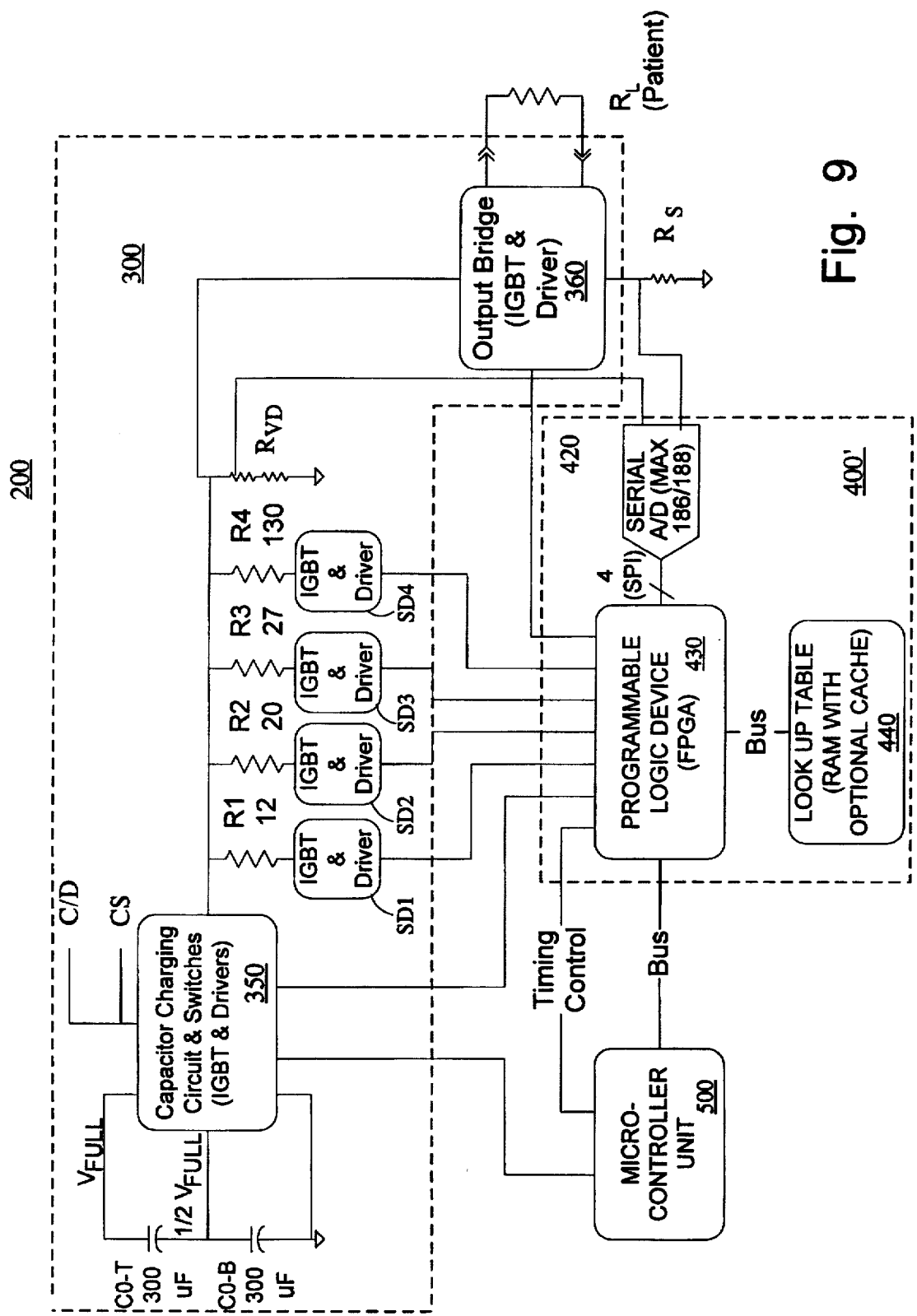
FIG. 9 is a detailed diagram of selected components of the electrophysiology diagnostic device system according to the present invention.

It should also be noted that the use of properly selected multiple PWM controlled resistors $R_1$–$R_N$, which may alternatively be denoted as "taps", advantageously can increase the dynamic range and achieve a more practical emulation of a variable capacitance C producing an exponentially decaying RC waveform, i.e., the exponentially decaying HV pulse, as discussed in greater detail with respect to FIGS. 5 and 9.

Figure 4:
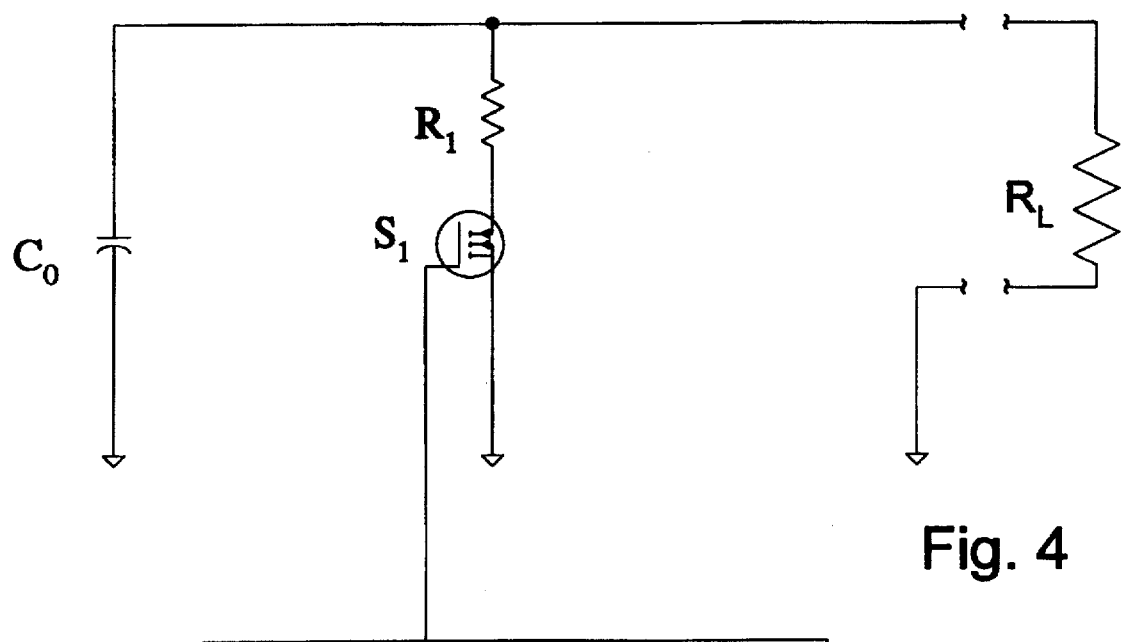
FIG. 4 is an exemplary circuit diagram which finds use in explaining the operation of a variable capacitance emulation circuit according to one aspect of the present invention illustrated in the block diagram of FIG. 3.
Figure 4:
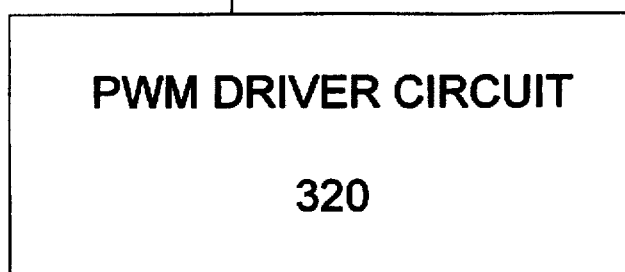

A practical implementation of the exemplary circuit depicted in FIG. 4, which would require several "taps" or PWM controlled resistors $R_1$–$R_N$ of various values to operate in an exemplary 6 to 1000 $\Omega$ target range for $R_{eff}$, is shown generally in FIG. 5 and specifically in FIG. 9. Referring first to the exemplary circuit according to a preferred embodiment of the present invention shown in FIG. 5, a plurality of resistive branch circuits are connected in parallel with both capacitor $C_0$ and load resistance $R_L$. Preferably, each branch circuit includes a fixed resistor $R_N$ and a corresponding switching element $S_N$, where N is a positive integer. In an exemplary case, each of the switching elements $S_N$ is electrically connected to a common PWM driver circuit 320', which advantageously generates switching signals at corresponding frequencies $f_N$. Preferably, each of the switch elements $S_N$ is a transistor switch and, most preferably, each of the switch elements $S_N$ is an insulated gate bipolar transistor (IGBT) switch. It will be appreciated that any number of parallel resistor—switch branch circuits can be located between $R_1$ and $R_N$. This circuit was developed to accommodate a given range of resistance for several important reasons, which reasons are discussed immediately below.

First, it should be noted that switching elements employing IGBTs would be required to handle the worst case voltage and current requirements of the VCE circuit 300 depicted in FIG. 5. Furthermore, it will be appreciated that the modulation rate of an IGBT is inversely proportional to the current through the IGBT, i.e., the higher the current, the slower the frequency of operation. Thus, an 850 Volt potential applied across a single 6 $\Omega$ resistor would produce a current of approximately 142 amperes. Assuming arguendo that a typical IGBT could handle that peak current, the maximum possible switching frequency $f_N$ for this current would be far below 1 kHz, i.e., 1 millisecond (msec). Since the worst case HV pulse would only last about 2 msec until a final value below 10% of the initial voltage was reached, it will be readily apparent that this switching frequency is far too slow. To prevent severe ripple and maintain reasonable control, it is preferable that each PWM controlled resistor $R_N$ be modulated using a modulation percentage in the range of about 10% to 90%, as discussed below.

Additionally, it will be appreciated that, in practical circuits, it is difficult to achieve PWM switching frequencies $f_N$ approaching 0% or 100%. This is especially true when the PWM switching frequency $f_N$ is high and On or Off periods on the order of a few microseconds are desired. For example, to achieve an effective resistance of 120 $\Omega$ using a 6 $\Omega$ resistor operating in accordance with equation (5) would require 5% modulation be produced by driver circuit 320'. Moreover, the output waveform would have a pronounced "stair-step" appearance resulting from a severe drop in the waveform voltage during the 5% modulation period.

In addition, it should be mentioned that the symbols used in depicting the IGBT switches $S_N$ in FIGS. 4 and 5 may be taken as portraying metal oxide semiconductor field effect transistors (MOSFETs) by those of ordinary skill in the art. This would be a harmless error since IGBTs and MOSFETs would, for purposes of this illustration, be interchangeable at any current below the MOSFET's $I_{MAX}$ limit.

Since the maximum operating frequency $f_{MAX}$ of the typical IGBT is inversely proportional to the current I conducted, several alternative circuit arrangements advantageously reduce the current $I_N$ through each respective IGBT switching element $S_N$, thus increasing the IGBT's maximum switching frequency $f_{MAX}$. The first such circuit arrangement would be to install multiple identical resistive branches instead of using a single branch. For example, two parallel resistive branches, each including a 12 $\Omega$ resistor would have an effective on-resistance of 6 $\Omega$ and each 12 $\Omega$ resistor would conduct only 71 Amps. Alternatively, the operating frequency of the IGBT advantageously can be increased by providing one or more high valued resistors, each of which could be selectively turned On or Off, in parallel with the PWM controlled resistor $R_N$. The solution of using different fixed resistor "taps" with the PWM controlled resistor $R_N$ for each resistance range would allow a practical circuit with reasonable modulation and, at the same time, would avoid severe ripple (noise) and other associated design problems.

A more elegant and novel circuit arrangement according to one aspect of a preferred embodiment of the present invention requires that multiple PWM controlled resistors taps are advantageously modulated simultaneously. Hereinafter, the expression resistor taps may be used to signify the resistors $R_1$–$R_N$, i.e., multiple resistors $R_N$. By modulating several resistors simultaneously, the dynamic range advantageously can be increased while maintaining a low part count. For example, PWM controlled resistor taps of 12, 20, 27 and 130 $\Omega$ would provide combinations of one or more resistors yielding resistive values including 5.6, 10.6, 11.5, 12, 17.3, 20, 22.4, 27 and 130 $\Omega$. See FIG. 9. This circuit arrangement is advantageously independent of the switching elements selected since it allows each of the resistors $R_1$, $R_2$, $R_3$, ..., $R_N$ to be a higher resistance value and thus be modulated at a higher frequency, i.e., the circuit arrangement carries less current for a given voltage.

A fundamental problem with the topology described above is that the worst case of a low patient impedance and a low capacitor emulation value requires a low PWM controlled resistor tap value (or composite PWM controlled resistors $R_1$ and $R_2$ values) which results in high IGBT currents $I_N$ and corresponding low switching frequencies $f_N$. Modulating multiple PWM controlled resistors $R_N$ allows the VCE circuit 300 to work well for the short decays with high peak currents as the "slow" PWM controlled resistors, e.g., $R_1$ and/or $R_2$, are augmented by "faster" PWM controlled resistors, e.g., $R_3$ and $R_4$, which faster PWM controlled resistors advantageously can keep the ripple down and maintain an output waveform with low error (noise or ripple). The above modulation technique for the VCE circuit 300 depicted in FIG. 5 helps minimize the constraints imposed by the physics of the selected switch.

It will be appreciated that the current limited switching frequency problem is typical of, but not limited to, IGBTs since physics shows that the switching rate will be limited for any electronic switch that has a less than instantaneous switching speed. This is due to the power absorbed by the device for each switching event and the ability of the device to dissipate the instantaneous and average power. The switching rate is thus limited by the device's instantaneous and average power capabilities, the switching speed (transition time) and the current density for each switching event. Thus, while the VCE circuit 300 according to a preferred embodiment of the present invention uses, in an exemplary configuration, IGBTs, the present invention is not limited to a particular switching element. Thus, other devices such as power MOSFETs and bipolar transistors advantageously can be used in place of the IGBTs discussed above.

Referring to FIG. 9, using available IGBTs to which a 850 Volt peak exponentially decaying waveform can be applied as switching elements $SD_N$, the 12 Ω tap can be modulated at 1 kHz (1 msec), the 20 Ω tap can be modulated at 5 kHz (0.2 msec) and the 27 and 130 Ω taps can be modulated at 10 kHz (0.1 msec) or more, as shown in the following table.

| Tap | Value (Ohms) | Modulation Frequency (kHz) | Modulation Period (µsec) |
|---|---|---|---|
| $R_1$ | 12 | ≤1 | 1000 |
| $R_2$ | 20 | 5 | 200 |
| $R_3$ | 27 | 10 | 100 |
| $R_4$ | 130 | 10 | 100 |

Once the topology of the VCE circuit 300 according to a preferred embodiment of the present invention was selected, it became reasonable to expect that there would be an optimal solution (algorithm) for modulating the available PWM controlled resistor taps. Stated another way, it seemed reasonable that since there are solutions that are considerably less than optimal, it follows that there should be some solution that is optimal.

When a resistance $R_{ef}$ is to be emulated using two or more resistor taps, the optimal PWM control needed to provide the minimum ripple (noise) is achieved through turning one resistor, or set of resistors, Off when the second resistor, or set of resistors, is turned On. The goal of the modulation technique for operating the VCE circuit 300 according to a preferred embodiment of the present invention is to permit switching between a resistance $R_1$ that is less than the target resistance $R_{ef}$ to a resistance $R_2$ that is greater than the target resistance $R_{ef}$, or vise versa, without generating a dwell or overlap period. Practical application in a system with two or more resistors preferably can be implemented using two or more PWM controlled resistors while any additional resistors remain either On or Off so as to provide an appropriate bias.

When using a multiple PWM controlled resistor tap scheme to emulate a variety of capacitor configurations reproducing exponentially decaying RC waveforms, the error or ripple preferably must be minimized. This is done to more closely emulate the ideal RC waveform, which is a smooth exponential decay, and to avoid "chopped" looking waveforms which would be unattractive to physicians monitoring the HV pulse. See FIGS. 10A through 10C and the corresponding discussion below. Ripple control also helps avoid the issue of possible second-order effects on the efficacy of the therapeutic HV pulse delivered to the patient due to significant noise (ripple) on the HV pulse. This modulation technique advantageously provides an optimal method of PWM controlling two or more resistor taps such that the error (ripple) between the ideal and emulated exponential RC decay waveforms is minimized. Additionally, this modulation technique advantageously facilitates the avoidance of narrow modulation pulse widths (near 0% and near 100%), which, as mentioned above, are difficult to reproduce with accuracy, when two or more PWM controlled resistor taps are used. Rigorous mathematical analysis confirms that all other modulation techniques will produce a greater error (ripple) under the same modulation constraints. Although this methodology applies to PWM control of two or more resistor taps, the exemplary case wherein two PWM controlled resistors $R_1$ and $R_2$ are used is the only case discussed at any length in the interest of brevity.

When a resistance $R_{ef}$ is to be emulated using two PWM controlled resistors $R_1$ and $R_2$, where $R_1 \leq R_{ef} \leq R_2$, then the optimal proportioning of the $R_1$ and $R_2$ PWM occurs when $R_{ef}$ is determined using $R_1/\alpha_1$ and $R_2/\alpha_2$ such that $\alpha_1 + \alpha_2 = 1$ where each $\alpha_i$ is a percentage of the period (T). Thus, $$R_{ef} = (R_1 * R_2) / ((\alpha_2 * R_1) + (\alpha_1 * R_2)) \tag{7}$$

which reduces to $$\alpha_1 = ((R_2/R_{ef}) - 1) / ((R_2/R_1) - 1) \tag{8}$$

assuming that $\alpha_2 = (1 - \alpha_1)$. Empirically, this is the case where a value of $R_2$ appears to always be in the circuit and a value of Re, where $R_1 = Re \| R_2$, is switched in for the minimum duration of $\alpha_1$ so as to achieve the required value of $R_{ef}$.

The case of $R_{ef} > R_2$ is a special case of the above general form where $R_1$ is off and another resistor $R_3$ appears to be so large that it has no effect with respect to $R_2$. Mathematically, this is stated as $\alpha_1 = 0$ and $\alpha_2 + \alpha_3 = 1$, where the value of $(R_3/\alpha_3) \rightarrow \infty$, so that $\alpha_3$ is essentially the time $R_2$ is off. Thus, the generic single PWM controlled resistor case using only $R_1$ reduces to a special case of the general form shown above where $R_2$ is very large ($\infty$). Similarly, for $R_{ef} < R_1$, a resistor $R_0$ can advantageously be emulated as $R_0 = R_1 \| R_2$ and can be handled as the case of $R_0 \leq R_{ef} \leq R_1$ using the general form shown above. In this case, the effect is that $R_1$ is always On ($\alpha_1 = 1$: during $\alpha_0$ for $R_0 = R_1 \| R_2$ and during $\alpha_1$ as just $R_1$) and $R_2$ is On only during the $\alpha_0$ period ($\alpha_2 = \alpha_0$) as $R_0 = R_1 \| R_2$.

When operating according to the above described modulation technique, as many parallel resistor taps may be used as needed in the VCE circuit 300 to expand the emulation range and/or provide greater dynamic range. This may be required to avoid too narrow modulation pulse widths, i.e., pulse widths approaching 0% or 100%, which pulse widths are, as mentioned above, difficult to produce with accuracy especially when only "slow" driver circuitry is required or achievable. It should be noted that there may be engineering trade-offs employed where only a few resistors are modulated while other resistors remain either On or Off to provide an appropriate offset or bias. For example, in the four resistor system illustrated in FIG. 9, two of the resistors, e.g., $R_2$ and $R_3$, advantageously may be modulated while the other two resistors, i.e., $R_1$ and $R_4$, provide needed bias. The choice of which two resistors are PWM controlled and how the other two resistors are used for establishing the needed bias would depend on the resistance $R_{ef}$ being emulated. In this fashion, any resistance from $R = R_1 \| R_2 \| R_3 \| R_4 / (0.9)$ to $R_4/(0.1)$ could be effectively emulated using 10% to 90% modulation providing that the resistors are properly selected to avoid dead bands in the desired resistance range.

It should also be noted that in systems employing electronic switches such as IGBTs, lower resistors values will conduct more current for a given voltage and thus need to be run at lower speeds. For each resistance range, the period is established by the slower of the resistor taps to be modulated. This would be the slower of $R_1$ and $R_2$ for $R_1 \leq R_{\text{eff}} \leq R_2$ and solely $R_2$ for $R_0 \leq R_{\text{eff}} \leq R_1$ and $R_{\text{eff}} > R_2$. Thus, it is desirable that $R_2$ be at least as fast as $R_1$, preferably faster. If multiple resistor taps are used, then the slowest of these resistors may be switched On to provide a bias that allows the above modulation technique to be used with reasonable speed and reduced ripple. For example, using values of 12, 20, 27 and 130 Ω would require that the 12 Ω resistor be on for $R_{\text{eff}} < \sim 11.4$ Ω to provide a suitable bias for emulating resistors in the range of ~5.8 Ω$\leq R_{\text{eff}} \leq$~11.4 Ω with a reasonably low error, i.e., ripple, as depicted in FIG. 12. It is important to note that for PWM controlled resistor taps in general, the higher the switching rate associated with a given one of the resistor taps, the less ripple that resistor will produce. However, it should also be noted that the modulation frequency of the lowest PWM controlled resistor, e.g., $R_2$, is preferably used when controlling all of the PWM controlled resistor taps.

As discussed above, when using a modulation technique employing PWM controlled resistor taps to emulate a variety of electrophysiology diagnostic device capacitor configurations, the error or ripple must be minimized to avoid "chopped" looking waveforms. A simple modulation technique that produces minimum ripple is desirable so that the "optimal" emulation using PWM control may be performed at each point. The optimal solution producing minimum ripple occurs for a resistance $R_{\text{eff}}$ to be emulated using two resistors $R_1$ and $R_2$, where $R_1 \leq R_{\text{eff}} \leq R_2$, when the following conditions are satisfied:

(a) $R_{\text{eff}} = R_1/\alpha_1 \| R_2/\alpha_2$; and (b) $\alpha_1 + \alpha_2 = 1$, where each $\alpha_i$ is a percentage of the period (T). Condition (a) can be rewritten in the form:

$$R_{\text{eff}} = (R_1 * R_2)/((\alpha_2 * R_1) + (\alpha_1 * R_2)) \quad (9)$$

which generates the solution $$\begin{aligned}\alpha_1 &= ((R_2/R_{\text{eff}}) - 1)/((R_2/R_1) - 1) \quad (10)\\ &= (((R_1 * R_2)/(R_2 - R_1)) * (1/R_{\text{eff}})) - (R_1/(R_2 - R_1))\end{aligned}$$

which, in turn, reduces to $$\alpha_1 = (a/R_{\text{eff}}) - b \quad (11)$$

where $$a = (R_1 * R_2)/(R_2 - R_1) \text{ and} \quad (12)$$

$$b = (R_1/(R_2 - R_1)) \quad (13)$$

Empirically, this is the case where a value of $R_2$ appears to always be in the circuit and a value of Re, where $R_1 = \text{Re} \| R_2$, is switched in for the minimum duration of $\alpha_1$ so as to achieve the required value of $R_{\text{eff}}$. The case of $R_{\text{eff}} > R_2$ is a special case of the above general form where $R_3$ appears to be so large that it has no effect with respect to $R_2$ and $\alpha_3$ is the "dwell" time of $R_2$. Thus, the generic single resistor PWM case using $R_1$ only reduces to a special case of the general form shown above where $R_2$ is very large (∞). Similarly, for $R_{\text{eff}} < R_1$, this case can be rewritten in the form $R_0 = R_1 \| R_2$ and handled as $R_0 \leq R_{\text{eff}} \leq R_1$ using the general form shown in equation (9) above. In this case, the effect is that $R_1$ is always on (during $\alpha_0$ for $R_0 = R_1 \| R_2$ and during $\alpha_1$ as just $R_1$) and $R_2$ is On only during the $\alpha_0$ period as $R_0 = R_1 \| R_2$.

As discussed in detail above, the patient impedance $R_L$ is assumed unknown since it is a complicated function of a given heart and ICD lead placements. In fact, it is a poor assumption that the patient impedance $R_L$ will remain constant from shock to shock due to possible repositioning of the leads to obtain more favorable thresholds and other patient parameters. Thus, it is required that the determination of $R_L$ must be made via a measurement at the beginning of each HV pulse event. Since the amount of energy delivered to a patient and the rate of change in the HV pulse voltage are greatest during the first portion of the exponentially decaying HV pulse, the patient impedance $R_L$ must be determined and emulation must be initiated as soon as possible to minimize excess energy delivery to $R_L$. This can be done by closely matching the voltage and energy density characteristics of the emulated HV pulse waveform with those of the desired (ideal) HV pulse waveform. For these reasons, the patient impedance measurement plays an important role in the success of the variable capacitor emulation circuit.

Assuming a worst case, i.e., an exemplary case where the HV pulse has an 850 Volt peak, $R_L = 15$ Ω, C=50 µF and $C_0 = 150$ µF, there will be approximately a 1 Volt error for each microsecond (µsec) of delay in initiating HV pulse emulation using the above described modulation technique. Since energy can not be placed back into the circuit once it has been absorbed by one of the PWM controlled resistor taps, it is a good assumption that the HV pulse emulation will begin with little or no PWM controlled resistance in the circuit until the patient impedance, i.e., load resistance $R_L$, can be determined or at least approximated. The extra energy may then be removed, if desired, by using a temporarily lower $R_{\text{eff}}$ achieved by PWM control of the resistor taps in the event that correction is deemed to be important.

Figure 10A:
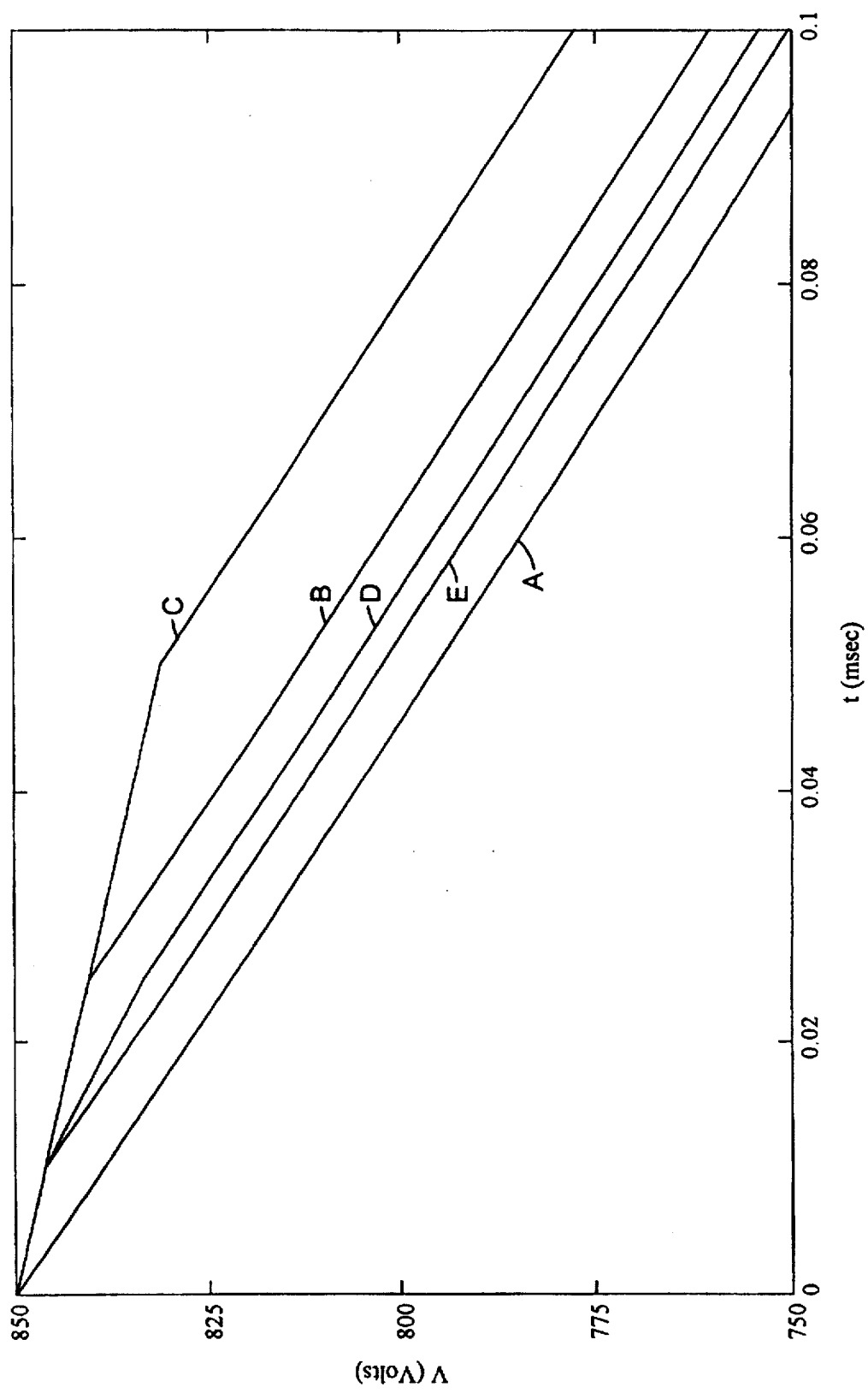
FIGS. 10A through 10C are computer generated plots which are useful in understanding the operation of the electrophysiology diagnostic device system illustrated in FIGS. 3 and 9.
Figure 10B:
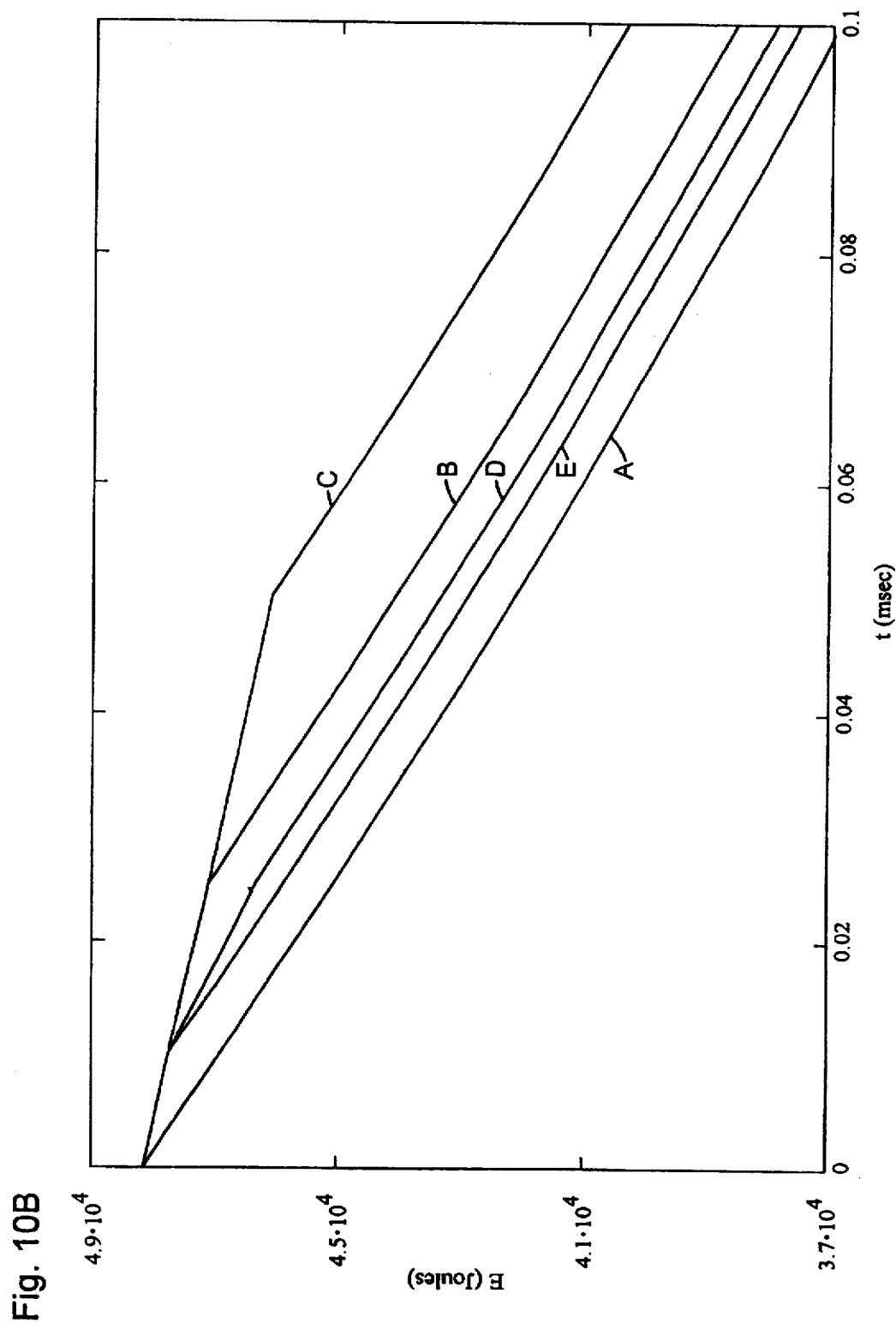
Figure 10C:
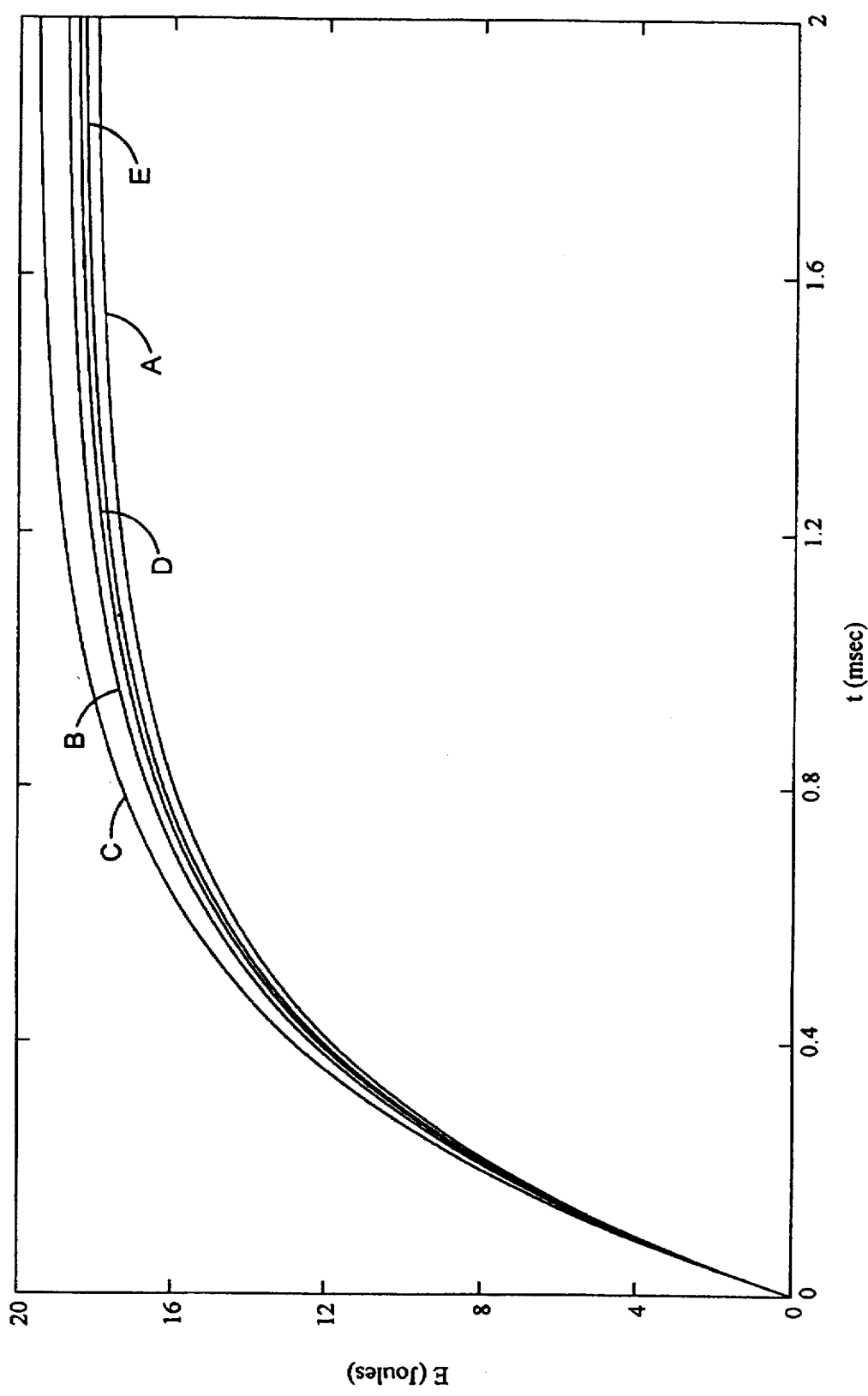

Irrespective of the approach used, the deviation between the ideal and the emulated HV pulse waveforms is proportional to the delay in initiating emulation correction, as shown in FIGS. 10A through 10C. FIG. 10A illustrates an ideal exponentially decaying HV pulse as curve A and a plurality of mathematically generated exponentially decaying HV pulses as curves B through E. Curve B depicts the exemplary case wherein the VCE circuit 300 operates to correct the emulated HV pulse at 25 µsec while curve C depicts an alternative case wherein the VCE circuit 300 operates to correct the emulated HV pulse at 50 µsec. In contrast, curve D illustrates HV pulse initial emulation initiated using a resistor $R_1$ operable at high speed followed by full HV pulse emulation after 25 µsec and curve E portrays HV pulse initial emulation initiated using resistor $R_1$ and $R_2$, both of which are operable at high speeds, followed by full HV pulse emulation after 25 µsec. By inspection, the worst case error between curve A and curves B through E occurs for curve C, generating an error of approximately 46 Volts at 50 µsec. Also by inspection, the minimum error between curve A and curves B through E occurs for curve E, generating an error of only about 10 Volts 10 µsec after the HV pulse is initiated. Curves A through E in FIG. 10B illustrate the instantaneous energy in Joules for each of the cases illustrated in curves A through E, respectively, in FIG. 10A. Curves A through E in FIG. 10C illustrate the integrated energy in Joules for each of the cases illustrated in curves A through E, respectively, of FIG. 10A. It will be appreciated that FIGS. 10A through 10C collectively illustrate the efficacy of initiating exponentially decaying HV pulse emulation by PWM control of resistor taps as soon as possible after the actual HV pulse begins.

It will be appreciated that in order to reduce the time required for determination of the PWM control parameters used by the PWM driver circuit 320', a lookup table (LUT) can be constructed where an initial value produced using shunt resistance $R_S$, after analog-to-digital conversion, is used as an input and the PWM control parameters for each of resistor taps are LUT outputs. It will also be appreciated that the calculation of the actual patient impedance $R_L$ is no longer directly required, since the LUT advantageously translates directly between a digital shunt voltage (A/D reading) indicative of current through load resistor $R_L$ and the PWM control parameters for the resistor taps. This advantageously allows for the fastest possible initiation of HV pulse emulation using the above described modulation technique, since the LUT allows all of the required PWM control parameter outputs to be obtained using a single unknown input, i.e., the voltage drop across shunt resistor $R_S$. It will be appreciated that the concept of using a LUT to speed critical algorithms is a standard practice used by those of ordinary skill in the art. However, it should also be noted that the use of a LUT storing PWM control parameters used in controlling a plurality of resistor taps to emulate a HV pulse has never before been described or suggested. Furthermore, since the modulation technique described above is a novel solution to emulating a resistance $R_{eff}$ which, in conjunction with a load resistance $R_L$ and a capacitor $C_0$, is used to emulate a capacitor C producing a desired exponentially decaying HV pulse across the load resistance $R_L$, the use of a LUT to store the PWM control parameters is likewise a unique and novel aspect according to the present invention.

It should be mentioned that the LUT 440 may be a separate RAM to speed the determination time when the bandwidth of the bus connecting MCU 500 and PLD 430 is limited, which is the condition shown in FIG. 9, or the LUT 440 may be incorporated into the RAM 530 of FIG. 3 when hardware costs or space considerations dictate or when the bandwidth of the bus connecting MCU 500 and PLD 430 permits. Moreover, the LUT 440 advantageously may function as a cache for data sampled by the serial A/D converter 420 during the HV pulse. See FIG. 9.

Using the above described techniques, the critical delay for reducing the voltage error between the actual and ideal HV pulses is the time from the initiation of the HV pulse until initiation of HV pulse emulation by PWM controlled resistor taps responsive to the initial shunt voltage $V_S$ value, e.g., the voltage value applied to the LUT. It will be appreciated that there are three components associated with this delay:

(a) the transient settling time;

(b) an A/D conversion period; and (c) a processing delay in applying the A/D output to the PWM controlled resistor taps.

When the HV pulse is initiated, there is a large transient as the output rises rapidly from zero volts to the peak HV pulse value, e.g., a worst case value of 850 Volts. Once this transient has settled, A/D conversion advantageously can be initiated using, for example, a track-and-hold circuit, so that a "clean" shunt voltage may be obtained. It will be appreciated that the delay required for proper settling is dependent on the final circuit design but the expected value is in the range of 5 to 10 µsec based on previous conventional designs. Thus, assuming that sampling can be started 10 µsec after the HV pulse is initiated, the A/D conversion and processing delays then become the critical factors yielding a delay in the HV pulse emulation. Thus, the total delay is on the order of 25 µsec when an associated LUT is incorporated into the RAM 530.

Figure 6:
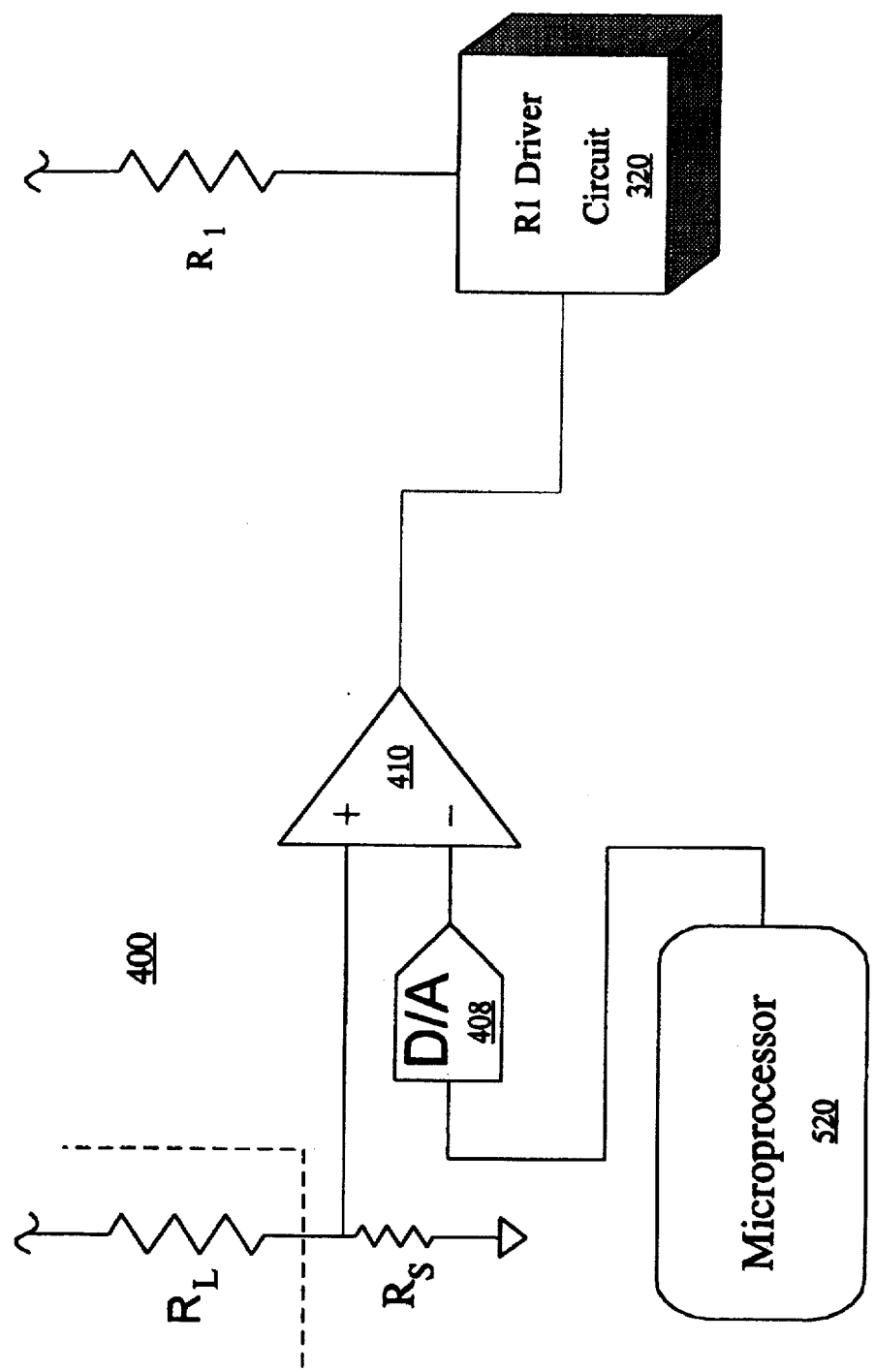
FIG. 6 is a detailed, partially schematic diagram illustrating a first preferred embodiment of the rapid response voltage threshold determination circuit according to another aspect of the electrophysiology diagnostic device shown in FIG. 3.
Figure 7:
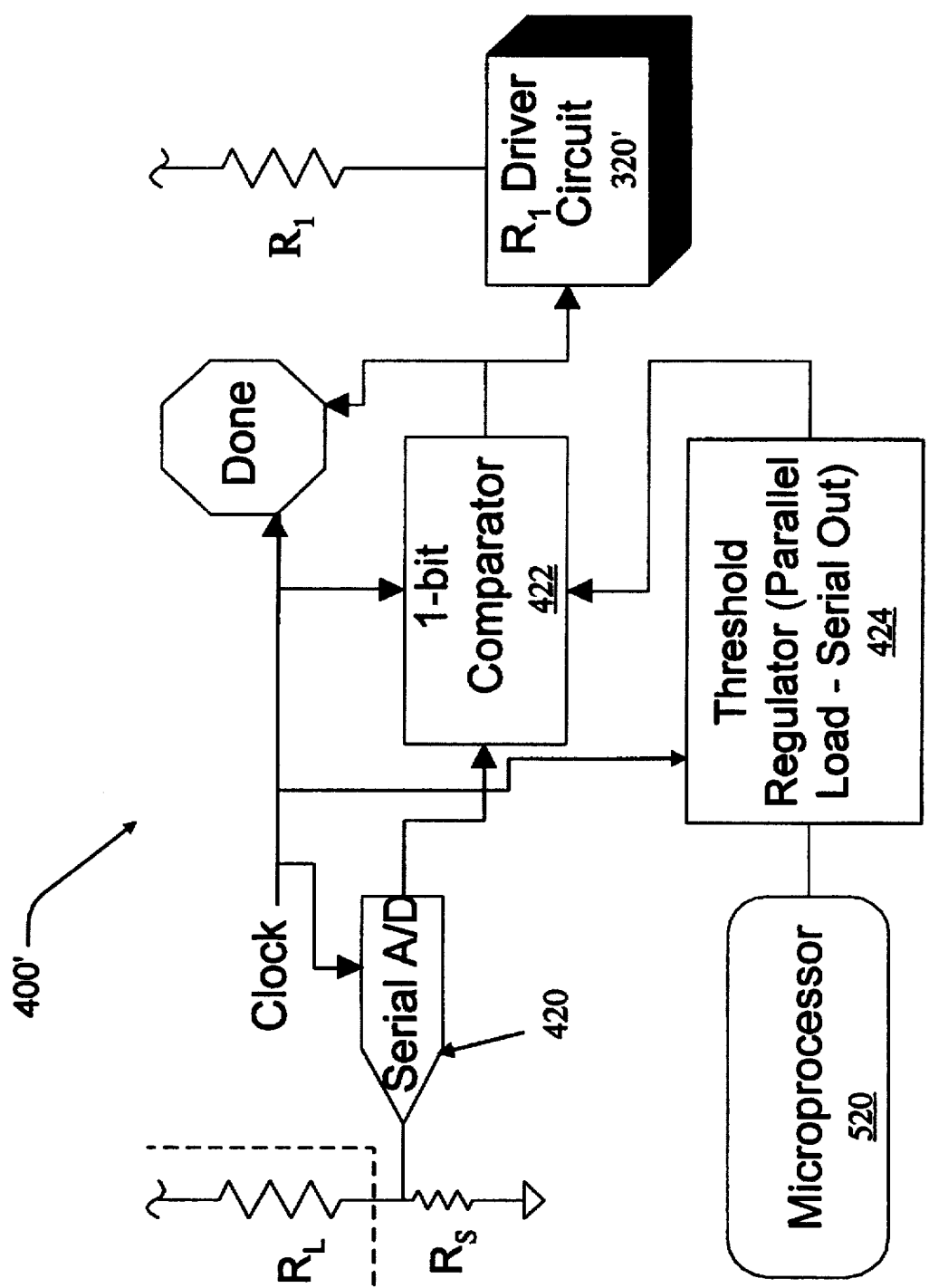
FIG. 7 is a detailed, partially schematic diagram illustrating a second preferred embodiment of the rapid response voltage threshold determination circuit of yet another aspect of the electrophysiology diagnostic device shown in FIG. 3.

The traditional approach for reducing this emulation delay involves the use of fast A/D converters and fast and/or custom hardware such as microprocessors, memories, such as the LUT 440 in FIG. 9, and field programmable gate arrays (FPGAs), e.g., this approach can be a very expensive way of providing a single fast HV pulse correction operation. The electrophysiology diagnostic device system according to the present invention, wherein preferred embodiments are shown, for example, in FIGS. 3 and 9, advantageously can employ one of two alternative comparator based RRVTD circuits, which are illustrated in FIGS. 6 and 7 and which are discussed in detail below, that capitalize on the effects of the lowest valued PWM controlled resistor of the resistor taps, i.e., resistor $R_1$. These alternative RRVTD circuits are important to the efficacy of the electrophysiology diagnostic device system as without correction a reasonable emulation delay of 25 µsec using conventional circuitry could ultimately generate an error of approximately 25 volts between the ideal and actual HV pulse waveforms for the worst case HV pulse.

In view of the discussion presented immediately above, it will be noted that the two alternative RRVTD circuits described below permit a rapid initial HV pulse emulation approximation, so that the error is reduced during the critical early portion of the exponentially decaying HV pulse. However, it should also be understood that these alternative approaches augment but do replace the conventional sampling method. In other words, the two alternative RRVTD circuits augment the conventional load resistance $R_L$ determination approach mentioned above by reducing the delay induced error.

Referring first to FIG. 6, an exemplary analog RRVTD circuit 400 includes a shunt resistor $R_S$ connected between load resistance $R_L$ and ground. The potential at $R_S$ is applied to a positive input terminal of a comparator 410; the negative input terminal of comparator 410 receives an ideal voltage threshold value from microprocessor 520 via DAC 408. The $R_1$ driver circuit 320 preferably receives the output signal from comparator 410, which output signal acts as the control signal needed to control the operation, i.e., turn On, of $R_1$ driver circuit 320. It will be noted that the use of an analog comparator 410 driven by DAC 408 permits comparison, at a specific time (t), of the actual HV pulse voltage with a programmed threshold voltage. It should also be noted that expansion of the RRVTD circuit 400 according to the analog preferred embodiment of the present invention requires a set of components including one DAC 408 and one comparator 410 for each threshold to be examined, i.e., 2N−1 sets for the determination of 2N−1 thresholds needed to control the operation of N PWM controlled resistor taps. In an exemplary case employing $R_1$ for rapid HV pulse emulation, resistor $R_1$ advantageously can be controlled responsive to a threshold denoting the voltage at which $R_1$ must go from On to Off or vice versa. It should further be noted that rapid HV pulse emulation using two resistors $R_1$ and $R_2$ requires three thresholds representing transitions between:

(a) [$R_1$ & $R_2$ On] and [$R_1$ On & $R_2$ Off];

(b) [$R_1$ On & $R_2$ Off] and [$R_1$ Off & $R_2$ On]; and (c) [$R_1$ Off & $R_2$ On] and [$R_1$ & $R_2$ Off].

The latter circuit configuration has the advantage of being fast while allowing all determinations to take place independent of the operation of an A/D converter (not shown) receiving the potential applied to shunt resistor $R_S$ and sampled after the initial 10 µsec stabilization delay.

The major drawback to this RRVTD circuit 400 is in the number of DAC—comparator sets required and the attendant additional discrete hardware components needed to support the DAC—comparator sets. For example, when emulation of an exponentially decaying HV pulse using more than one resistor $R_N$ is being performed, a logic element is required to gate the $R_N$ resistor driver circuit 320 appropriately based on the inputs obtained from all of the DAC—comparator sets. It should be noted that the thresholds are determined in such a way that the PWM controlled resistor taps selected for HV pulse emulation are to remain on until some time after the critical delay. For example, the modulation technique with $R_1$ and $R_2$ On initially may leave $R_1$ On throughout the HV pulse emulation and turn $R_2$ Off at 40 μsec as part of the $R_2$ modulation required for that HV pulse emulation. It will be appreciated that the design of the comparator circuitry for the implementing the above described modulation technique is a task suited to those of ordinary skill in the art of circuit design and is not shown or described here.

The preferred embodiment described immediately above would be considered a more traditional approach to the problem of fast HV pulse emulation approximation. With a constant 10 μsec determination, the worst case error is just 10 Volts (≈1%) versus 25 Volts (≈3%) for a delay of 25 μsec before emulation.

Referring to FIG. 7, an alternative digital RRVTD circuit 400' includes the shunt resistor $R_S$ connected between load resistance $R_L$ and ground. The potential applied to $R_S$ is also applied to a serial analog-to-digital (A/D) converter 420. The digital bits generated by the serial A/D converter 420 are applied to a one bit digital comparator 422, which advantageously receives bits from the microprocessor 520 via a threshold register 424. Preferably, register 424 receives parallel bits from microprocessor 520 and serially outputs these bits to comparator 422. The output of comparator 422 advantageously controls the switching of PWM controlled resistor $R_1$ via $R_1$ driver circuit 320'.

Figure 8:
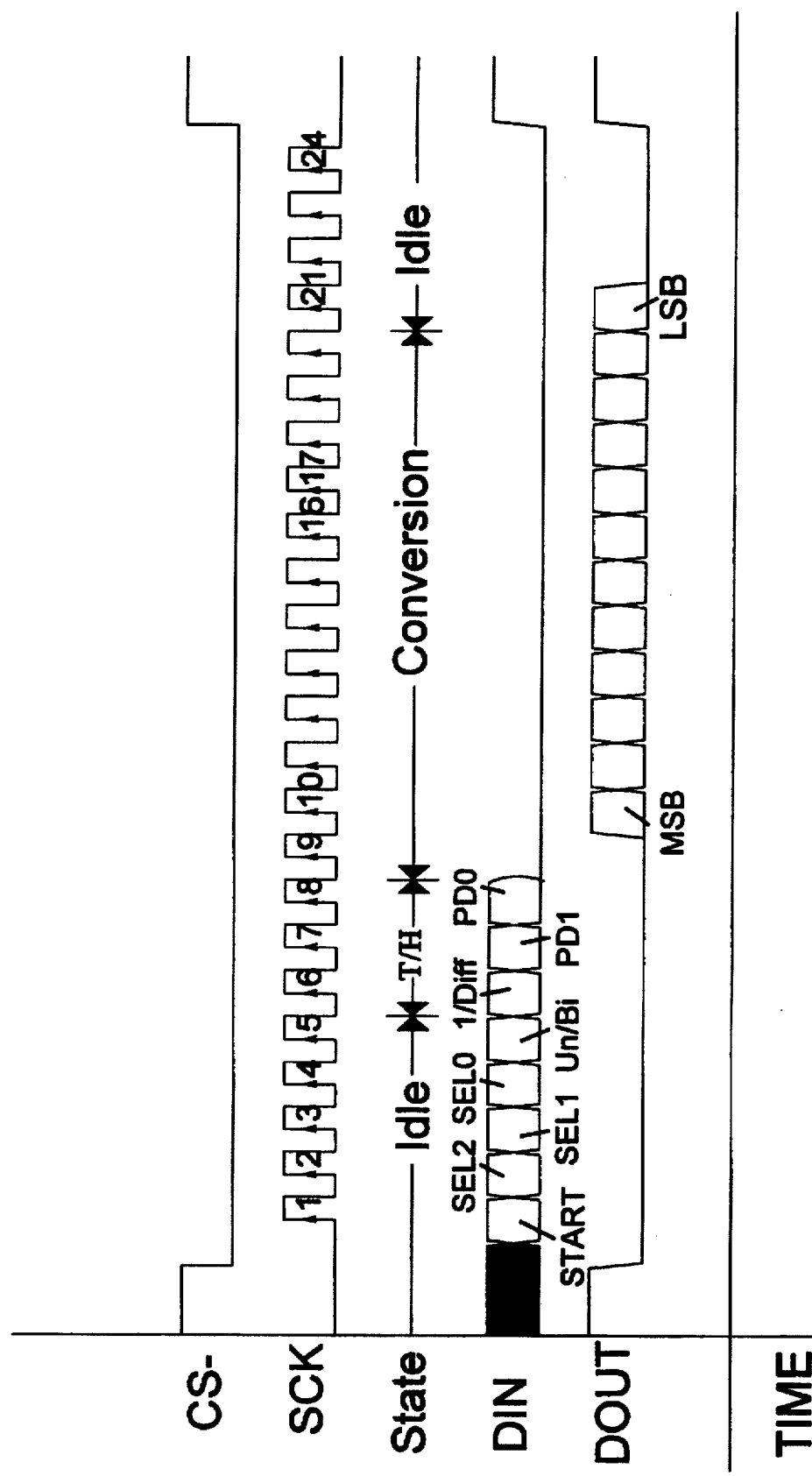
FIG. 8 illustrates several waveforms which are useful in understanding the operation of the circuit illustrated in FIG. 7.

The digital RRVTD circuit 400' capitalizes on the effects of the lowest valued PWM controlled resistor, i.e., $R_1$, coupled with serial successive-approximation A/D converters such as the so-called Maxim MAX186 or MAX188 devices. It should be noted that the MAX186 and/or MAX188 timing diagram shown in FIG. 8 will be used for all subsequent descriptions of the RRVTD circuit 400' shown in FIG. 7. With reference to FIG. 8, a 2 MHz A/D clock (SCK) is assumed, thus providing a 0.5 μsec per bit timing.

As can be seen from the "State" signal in FIG. 8, the A/D has an internal Track-and-Hold (T/H) circuit which begins tracking on the falling clock edge (SCK) after the fifth bit of the 8-bit control word has been shifted in (DIN) following the active low "CS-" signal. The internal T/H circuit enters its hold mode on the falling clock edge (SCK) after the eighth bit of the 8-bit control word has been shifted in (DIN). Again, assuming a sample at 10 μsec as stated above, the first control bit can be clocked to the serial A/D converter 420 just 6 μsec after the actual HV pulse begins ($t_0$+6 μsec). Thus, the sample is held in the serial A/D converter 420 at 10 μsec and the most-significant-bit (MSB) of data is available 0.5 μsec later. Advantageously, a new data bit is available each 0.5 μsec until the complete A/D value has been shifted out at 16 μsec. When the complete A/D value is available, the microprocessor 520 of FIG. 3 or the MCU of FIG. 9, for example, may begin determination of the PWM parameters as described above and full PWM control should begin on the order of 25 μsec after the HV pulse has begun, i.e., a reasonable delay, as was assumed previously.

Referring again to FIG. 7, the digital RRVTD circuit 400' compares the serial output from the serial A/D converter 420 to a threshold representing the voltage. The comparator 422 need compare only one bit as the data arrives from the serial A/D converter 420 in a serial fashion with the MSB arriving first. Once a 1-bit comparison has established an inequality, the whole comparison is essentially determined based on that single bit. It should be noted that this is a feature of any algorithm or circuit that compares the MSB first and moves seriatim toward the least-significant bit (LSB).

It should be noted that expansion of the RRVTD circuit 400' according to the digital preferred embodiment of the present invention requires a comparator 422—register 424 set for each threshold to be examined, i.e., 2N−1 sets for the determination of 2N−1 thresholds needed to control the operation of N PWM controlled resistor taps. In an exemplary case employing only $R_1$ for rapid HV pulse emulation, resistor $R_1$ advantageously can be controlled responsive to a threshold denoting the voltage at which $R_1$ must go from On to Off or vice versa. Rapid HV pulse emulation using two resistors $R_1$ and $R_2$ again requires three thresholds representing transitions between:

(a) [$R_1$ & $R_2$ On] and [$R_1$ On & $R_2$ Off];
(b) [$R_1$ On & $R_2$ Off] and [$R_1$ Off & $R_2$ On]; and
(c) [$R_1$ Off & $R_2$ On] and [$R_1$ & $R_2$ Off].

The latter circuit configuration has the advantage of being fast while allowing all determinations to take place independent of the operation of the serial A/D converter 420 receiving the potential applied to shunt resistor $R_S$ and sampled after the initial 10 μsec stabilization delay.

It should also be noted that the comparator 422 advantageously can set any appropriate flags including a done bit signifying an inequality, completion of a full count, greater than, less than and, if desired, an equality. It will be appreciated that, for a one bit comparator, equality is not established until a counter sets the done bit while inequality flags are not set. Of course, determining an equality takes the same amount of time as a conventional parallel A/D device coupled to a digital word comparator when the full A/D resolution is required. This is only a concern when the input matches the threshold for "$R_1$ Only" and the "$R_2$ Only" signal is delayed until the equality is established. The equality need not be established with the full resolution of the serial A/D converter 420; one could choose to restrict all comparisons to some smaller number of bits (6 to 10) to speed determination at the expense of threshold resolution. This worst case determination still eliminates the processing delay and has a far smaller impact than that found for the worst case HV pulse.

The advantage of the digital RRVTD circuit 400' depicted in FIG. 7 is that it uses less hardware than the analog RRVTD circuit 400 shown in FIG. 6, particularly as the comparator 422 may be included in the same FPGA (or comparable device) as the logic required to gate the PWM resistor driver 320', as well as portions of the driver itself, illustrated in FIG. 5. Once one of the PWM controlled resistor taps has been determined, i.e., a threshold comparison is complete, the digital RRVTD circuit 400' functions identically to the analog RRVTD circuit 400.

It will be appreciated that the principal disadvantage of the digital RRVTD circuit 400' is that the comparison time for each threshold is non-deterministic, i.e., determination takes from one to M bits, where M is 12 or less, for the MAX 186/188. This is not as large a disadvantage as one might first think, since the rate of determination is proportional to the difference between the actual HV pulse at time (t) and the threshold voltage representing the ideal HV pulse. Thus, this difference or error is directly proportional to the error between the actual and ideal signals. For example, the worst case HV pulse will produce a large HV pulse to threshold difference, causing operation parameters for PWM controlled resistors $R_1$ and $R_2$ to be determined quickly, while a HV pulse emulated using PWM controlled resistor $R_2$ only, which is right on the "$R_1$ Only" threshold, will take the full bit count for determination. Given HV=850 Volt peak, $R_L$=28 Ω, C=50 μF and $C_O$=172.5 μF, and assuming that the PWM resistance $R_{eff}$ is on the $R_1$ threshold of 11.4 Ω, there is a 7 Volt (~1%) error when emulation is delayed for 16 μsec, assuming a full 12-bit comparison rather than a shorter 6 to 10 bit comparison. Due to the nature of this method, the maximum error for a)l cases can be restricted to the worst case error of ≈10 Volts (≈1%) for a correction started at ≈10 μsec.

It is worth noting that the threshold resolution, i.e., the number of bits compared, need not be constant. The resolution can be established for each emulation once the peak HV pulse voltage and emulation capacitance (C) are known. This advantageously could be accomplished using a simple register and variable length counter, circuitry very familiar to those of ordinary skill in the art of digital design. This dynamic threshold resolution may be considered to be important as the peak HV pulse value drops and finer resolution is required for threshold comparisons.

FIG. 9 illustrates a more detailed preferred embodiment of electrophysiology diagnostic device 200, which preferably includes a VCE circuit 300' having a pair of 300 μF capacitors $C_{O-T}$ and $C_{O-B}$ connected to a capacitor charging circuit and switches module 350, and a plurality of PWM controlled resistors $R_1$-$R_4$, each of these resistors being connected in parallel with load resistor $R_L$ via output bridge module 360. In FIG. 9, the driver circuit 320' and switches $S_1$-$S_N$ depicted in FIG. 5 are depicted as a consolidated switch and driver circuit $SD_N$, where $SD_N$ controls PWM controlled resistor $R_N$, respectively. The electrophysiology diagnostic device 200 preferably also includes a RRVTD circuit 400' including the serial A/D converter 420, a programmable logic device (PLD) 430, which PLD preferably includes a 1-bit comparator (See FIG. 7.), operatively connected to a lookup table (LUT) 440. As discussed in greater detail below, the module 350 and the PLD 430 are operatively connected to and operated by microcontroller unit (MCU) 500.

In an exemplary and non-limiting case, the electrophysiology diagnostic device 200 is constructed according to the following specifications:

15≤$R_L$≤120 Ohms;

50≤C≤120 μF (for emulation where C=$C_O$ for 150 μF Nominal);

$C_O$=$C_{O-T}$+$C_{O-B}$=150 μF+20%, −10% (135≤$C_O$≤180 μF);

$C_{O-T}$=300 μF+20%, −10% (270≤$C_O$≤360 μF);

$C_{O-B}$=300 μF+20%, −10% (270≤$C_O$≤360 μF);

50≤$V_O$≤850 Volts; and $R_S$=0.0626 Ω≈1/16(+0.16%).

It should be noted that the modulation techniques described above are intended to be used with a fast, powerful MCU 500, such as a Motorola MC68332 device or a ColdFire (52xx) device. It should also be mentioned that there are two basic control approaches: open loop control; and closed loop control. The open loop approach uses a single impedance measurement to determine the PWM control parameters used during the entire HV pulse. An MC68332 has sufficient processing speed and power for this approach. Closed loop control updates the PWM control parameters based on a series of impedance measurements so as to reduce error and compensate for possible changes in patient impedance and capacitor voltage-related non-linearities. If the loop is loosely closed, i.e., data updates occur only occasionally, the MC68332 may be a sufficient for the task. However, if the control loop is tightly closed, i.e., data updates occur frequently, the more modern Cold-Fire (52xx) class of MCU may be required to provide the necessary performance and margin. In an exemplary case wherein the control loop is tightly closed, values at both shunt resistor $R_S$ and voltage divider $R_{VD}$ are alternately sampled using a switch (not shown) connected to the serial A/D converter 420 during each loop cycle.

Preferably, the module 350 is under MCU 500 control with the exception that charge/deliver (C/D) and capacitor selection (CS) control signals are externally produced. When a therapeutic HV pulse is to be delivered, the C/D control signal is set to a deliver mode of operation, which impedes charging. This control signal returns module 350 to the charge state after the HV pulse is terminated, provided an error has not occurred, e.g., the signal is then used to prevent the capacitors $C_{O-T}$ and $C_{O-B}$ from recharging. The CS control signal advantageously selects between $C_O$=$C_{O-T}$ in series with $C_{O-B}$, which thus produces an effective 150 μF capacitor or $C_O$=$C_{O-B}$, which results in an actual 300 μF capacitor being used to deliver the HV pulse.

Advantageously, output bridge module 360 allows the patient load resistance $R_L$ to be connected in such a manner that either a positive or a negative HV pulse is selectively delivered. It should be noted that since the actual capacitor values and the shunt current and associated voltage drop are always positive, the serial A/D converter 420 may advantageously use a unipolar (positive) input.

Referring specifically to FIG. 9, the MCU 500 sets the PLD 430 to a delivery mode of operation via the data bus and then uses the Timing Control (TC) signals to initiate a HV pulse event. This advantageously allows the MCU 500 to be isolated from the precise timing requirements of the delivered HV pulse. For fault conditions, the MCU 500 provides the ability to terminate the delivered HV pulse at any time by de-asserting the TC signals.

The LUT 440, which may in an exemplary case be a RAM, is controlled by the PLD 430 so that during delivery of the HV pulse, the appropriate PWM parameters advantageously may be established. The LUT 440 preferably is loaded by the MCU 500, as discussed in greater detail below, in a write-through fashion and may be verified in a read-through fashion. In an exemplary case, the LUT 440 may be viewed as a multi-dimensional array with the initial shunt voltage $V_S$ measurement, which corresponds to current applied to the patient's heart, used as the index. Tabled values include the PWM configuration and the $\alpha_1$ (first duty factor) for each period T. When using the optimal PWM modulation technique, one PWM controlled resistor, e.g., $R_1$, is On for the initial $\alpha_1$ portion of the operating period T, the operated resistor $R_1$ then it is turned Off and another PWM controlled resistor, e.g., $R_2$, advantageously may be switched On for the remainder, $\alpha_2$, of the period T. This is equivalent to the duty factor with the first tap modulated. The period T may also be stored as a table value or it may be determined from the PWM controlled resistor taps being modulated. To save space while increasing the operating speed of the LUT 440, the PWM control configuration advantageously may be stored in a single byte. Each bit of the byte would identify whether a given resistor is On during the $\alpha_1$ portion or the $\alpha_2$ portion of the period T. The Table presented immediately below depicts an exemplary byte wherein a 1 in a given bit position would turn the corresponding one of the resistor taps On for the indicated portion of the period T. Preferably, a count value corresponding to the $\alpha_1$ portion of the period T is stored as a second byte in LUT 440. Thus, the first byte specifies which of the resistor taps transition between On and Off states while the second byte specifies the time after the start of period T at which all transitions occur.

It should be noted that since the lowest resistance $R_1$ is approximately 12 Ω, $R_1$ will generally be too slow to be modulated. Consequentially, the $\alpha_1$ and $\alpha_2$ pair of values would always be either "00" or "11". A value of "11100100" would denote that $R_1$ is always on, $R_2$ is turned On during the $\alpha_1$ portion of period T only, $R_3$ is turned on during the $\alpha_2$ portion of period T only and $R_4$ would remain off during the whole period T. This corresponds to ID No. 8 for $R_1$ On (7.57 to 8.22 Ω range), as shown in FIG. 12.

| $R_1$ | | $R_2$ | | $R_3$ | | $R_4$ | |
|---|---|---|---|---|---|---|---|
| 1 | 1 | 1 | 0 | 0 | 1 | 0 | 0 |
| $\alpha_1$ | $\alpha_2$ | $\alpha_1$ | $\alpha_2$ | $\alpha_1$ | $\alpha_2$ | $\alpha_1$ | $\alpha_2$ |

Figure 11:
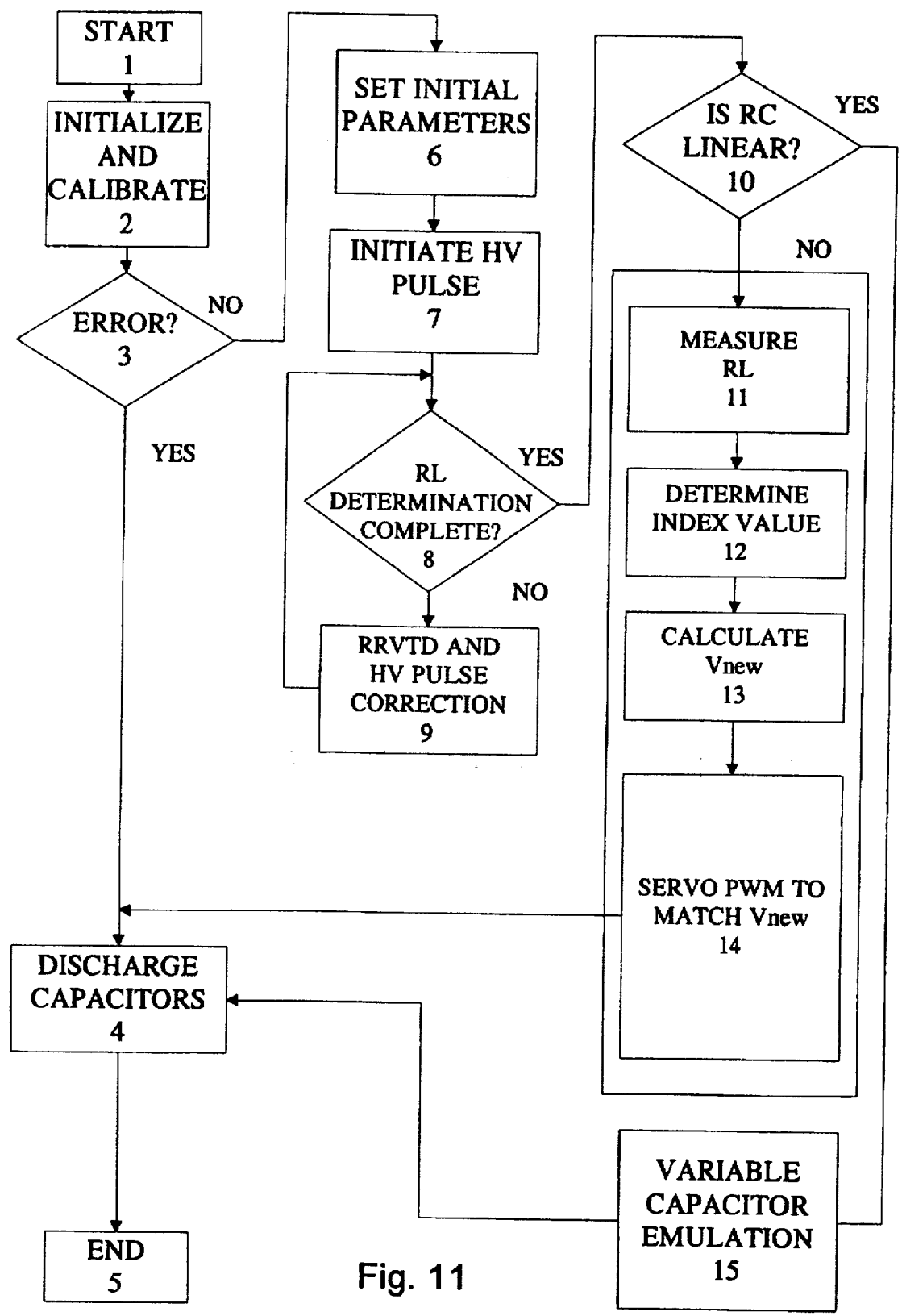
FIG. 11 is a flow chart depicting the operational steps performed by the electrophysiology diagnostic device of FIG. 9 both preceding and during a HV pulse event.

The operation of electrophysiology diagnostic device 200, as illustrated in FIG. 9 will now be described while referring to both FIG. 9 and the flow chart of FIG. 11. It will be appreciated that the electrophysiology diagnostic device system described thus far advantageously can emulate a variety of HV pulses corresponding to source capacitance C values in the range of approximately 50–150 μF, preferably in 1.0 μF steps, in combination with a variable load resistance $R_L$ in the range of approximately 15–120 Ω, in 1 Ω steps. Preferably, the electrophysiology diagnostic device system 200 can emulate the HV pulses produced by ICDs with non-linear capacitance C values that change by approximately 20% or more with voltage. The technique illustrated in the flow chart of FIG. 11 allows the electrophysiology diagnostic device system output to be driven in such a way as to emulate variable and non-linear capacitance C values with a variable load resistance $R_L$ i.e., non-linear RC characteristics as discussed below.

During step 1, electrophysiology diagnostic device 200 is energized and allowed to warm up as needed. Then, electrophysiology diagnostic device 200 is initialized and calibrated to determine, for example, the actual values of $C_{0-T}$ and $C_{0-B}$ and proper operation of the respective IGBTs in $SD_1$ through $SD_N$, during step 2. It should be noted that output module 360 preferably is disabled during the calibration operation.

Preferably, the PWM controlled "taps" can be used in calibrating the circuitry and determining the value of $C_0$, i.e., $C_{0-T}$ and $C_{0-B}$, such that $C_0$ is either $C_{0-B}$ alone or $C_{0-T}$ in series with $C_{0-B}$ depending on the state of the CS control signal. During step 2, the capacitor bank $C_0$ is first charged to its maximum voltage value. A check is then made for current flow through the shunt resistor $R_S$; if current flow is detected through $R_S$, then a failure in the IGBT output switch in output bridge module 360 is detected, nominally during performance, i.e., interrupt performance, of step 3 and declared, the charging operation is aborted, $C_{0-T}$ and $C_{0-B}$ are discharged during step 4 and operation ends during step 5. In short, electrophysiology diagnostic device 200 disables itself upon detection of a predetermined error condition in any one of the electrophysiology diagnostic device 200's primary subsystems.

Still referring to step 2, a full voltage (150 μF, $V_{FULL}$) HV pulse is initiated, thereby disabling the capacitor charging circuit. Then, beginning with the lowest valued tap, $R_1$, each of the four taps $R_1 \ldots R_4$, are activated for 1 msec and the initial and final voltages for each such activation are recorded. Immediately following the recording of the voltage Vf4, a half voltage (300 μF, ½ $V_{FULL}$) HV pulse will then be initiated, i.e., the capacitor charging circuit remains disabled, and then, beginning with the lowest valued tap, each of the four taps is again activated for 1 msec and the initial and final voltages will again be recorded.

The values of $C_0$, $C_{0-T}$, and $C_{0-B}$, assuming 10% or less precision, advantageously can then be determined (calculated) in numerous ways, e.g., as the average of the values from each of the previous eight discharges. It should be noted that the taps, i.e., the PWM controlled resistor taps have a precision ≦1%. Since the uncertainty (noise) of a value follows the square root of the number of samples, the capacitor $C_0$ values can be determined to within about 0.5% with a 1% maximum error when 1% tap resistors are used. Advantageously, the tap resistance values may then be adjusted accordingly for consistency. This should determine the tap resistance values within 0.5% average error with a 1.5% worst case actual error within the ±1% error window. When the capacitor $C_0$ or resistor taps have values which are determined to be outside the manufacturer's specification, i.e., the error is greater that 1% for any of the PWM controlled resistor taps, then an error will be identified at step 3 and the electrophysiology diagnostic device 200 will shut itself down at step 5 after performing step 4. It should be noted that an alternative technique would be to provide and make use of the above-described calibration technique but using a much higher precision tap (0.1%) for calculating the above values. Ideally, this would be the highest valued tap, i.e., the 130 Ω resistor $R_4$, so that the effects of the switching circuit $SD_4$ would be minimal.

Still referring to step 2, when a HV pulse, or a portion thereof, has been completed, and the appropriate signals have been asserted or de-asserted, then the electrophysiology diagnostic device 200 system hardware is monitored for output IGBT failures. If either the capacitor voltage $V_c$ is changing, i.e., discharging, so that two consecutive samples are not within some noise margin, or the shunt resistor current is not approximately zero, e.g., some very small value below a noise margin, then the output bridge module 360 is determined to be malfunctioning. It will be appreciated that the later situation indicates that energy is being applied to the patient, i.e., $R_L$. In that event, all PWM controlled resistor taps are commanded On during step 4 and the electrophysiology diagnostic device 200 turns itself Off during step 5. Step 4 thus acts as electrophysiology diagnostic device 200's "Emergency Brake", as discussed in greater detail below. If an error is not identified during step 3, the electrophysiology diagnostic device 200 proceeds to step 6.

It should be noted turning On all of the resistor taps simultaneously acts to drain the capacitor $C_0$ stack through the PWM resistor taps with the minimal energy going to the load ($R_L$). This is equivalent to pulling the Emergency Brake on a train; it does not stop the train immediately but it is the best that can be done. It should also be noted that if the output IGBT has failed short then the output will not drop to zero immediately; it will decay towards zero very quickly with a minimal "overdose" of energy to the patient.

It should be mentioned that to facilitate construction of multiple LUTs based on different capacitance and voltage parameters, an intermediate $R_{ef}$ range table advantageously can be constructed. This range table would be solely a function of the tap values determined through calibration and represents the optimal configuration type for a small portion of the total emulation range of $R_{ef}$. The range table preferably is constructed by comparing each valid configuration type for the given small range of emulated resistances and identifying the configuration type that provides the least error, i.e., ripple.

Recalling that the electrophysiology diagnostic device 200 load impedance $R_L$ is not known at the beginning of each therapeutic HV pulse, it may be assumed that the sequential therapeutic HV pulses have very similar $R_L$s. However, modifications to the lead system such as repositioning a lead or adding a patch electrode would invalidate that assumption. The "fix" of having the operator prompted to enter an initial $R_L$ estimate has several drawbacks including the added complexity to the user interface, the increased potential for operator error, and an unknown actual value that may vary with the therapeutic HV pulse.

When the initial capacitor voltage $V_0$ is programmed during step 6, the LUT 440 advantageously can be loaded with a table of initial resistance estimate values so that, at time $t_0$ when the initial output current shunt voltage $V_S$ is sampled ($\approx$5 to 10 µsec after $t_0$), the initial $R_L$ estimate can be quickly taken from this table. Preferably, the table could be constructed using the simple equation $$R_L \equiv V_0/I = (V_0 * R_S)/V_S \quad (14)$$

where $V \equiv V_0$ to the first order at time $t_0$. The index to the table is $V_S$ as a truncated byte value for 0.5 Ω resolution (128 Ω/256). The second order equation where $$R_L = V/I = (V*R_S)/V_S \text{ (where } V \neq V_0) \quad (15)$$

is easily calculated using the voltage drop from the table of $e^{-t/\tau}$, as described in greater detail below, and the small voltage drops associated with any peripheral circuitry such at the output bridge module 360 and the shunt resistor itself. It will be appreciated that for a 0.1 Ω shunt resistor $R_S$ carrying 56 Amps, the voltage drop will be only 5.6 Volts. For a 15 Ω $R_L$ and a 50 µF (worst case), an estimate of 15.3 Ω, where the actual $V=(0.987*V_0)-V_S$ is used when calculating $V_S$ at 10 µsec, represents only a 2% error. For 120 Ω $R_L$ and a 150 µF (best case), the estimated load resistance $R_L$ is 120.2 Ω which is a 0.1% error. It seems reasonable that an initial estimate of 2% is sufficient to begin the PWM correction process. Subsequent sampling of $R_L$ as calculated from $V_S$ and the actual output voltage (V) advantageously can provide much better resolution and control during the therapeutic HV pulse and would compensate for any noise induced effects.

Moreover, during step 6, the operator selects a capacitance table, which is a simple array mapping capacitance values with indexing in volts. In an exemplary case, the capacitance is determined at 10 Volt increments, e.g., a 0 to 850 Volt range contains indexes ranging from 0 to 85. It will be appreciated that if a linear capacitance is to be emulated, then the capacitance table will have a constant capacitance C in all locations. Then, a capacitance index table (CIT) is generated by subtracting the lowest capacitance value from each value in the capacitance table. The CIT is then used in generating a table of $e^{-t/\tau}$ values, the use of which is discussed in greater detail below.

Moreover, during step 6, a decay table of values $e^{-t/\tau}$ for all of the various RC combinations is generated so that each 10 µsec a new output voltage can be calculated using the formula $$V_{new} = V_{last} * e^{-t/\tau}. \quad (16)$$

It will be appreciated that the decay table advantageously can be built using a truncated Taylor series where $$e^x = 1 + x + x^2/2! + x^3/3! + x^4/4! + \ldots \quad (17)$$

which can be is approximated as $$e^x = 1 + x + x^2/2! + x^3/3! \quad (18)$$

It should be noted that this algorithm uses 16-bit words, where the resultant 16-bit word is accurate to one part in 2.5 million (0.4 PPM) for the worst case, i.e., $R_L$=15 Ω and C=50 µF. It should also be noted that it is important to use 32-bit math as the round-off error for 4000 iterations used in modeling a 20 msec HV pulse can be significant when $e^x \approx 0.99$, even when only four Taylor series terms are used.

Finally, the HV pulse is initiated during step 7 and sampling of the potential across shunt resistor $R_S$ begins. During step 8, a determination is made as to whether the load resistance $R_L$ has been determined completely. In an exemplary case, the load resistance sampling is said to be completed when the entire output word from an A/D device, preferably the serial A/D converter 420, is available. When less than the entire output word is available, operational control passes to step 9. During step 9, the RRVTD circuit 400', for example, determines whether an error between the actual and ideal HV pulse waveforms has occurred on a bit-by-bit basis. When an error is identified, PLD 430 activates at least one of the elements $SD_1$-$SD_4$ in order to begin correction of the actual HV pulse waveform as soon as possible, as discussed above and in greater detail immediately below. When the current 1-bit comparison has been completed, the operating sequence loops back to the start of step 8.

During step 9, the digital bit stream corresponding to the potential at $R_S$ generated by A/D converter 420 is applied to three one bit comparators included in PLD 430. Each of the one bit comparators receives a threshold voltage value from a respective register so that the bit stream corresponding to the actual waveform can be compared with the three thresholds simultaneously. The three values of $V_S$ are then written to the FPGA, i.e., PLD 430, for use by the RRVTD circuit 400', which is described in greater detail above. Thus, the $V_S$ values corresponding to the transitions between the various PWM control modes of operation advantageously can be used to determine whether an error needing compensation is occurring and the specific ones of the PWM controlled resistor taps best suited to deal with the error. It should be mentioned that the values associated with the PWM control configuration are optional for the RRVTD circuit 400' since the PWM control configuration stored in connection with the RRVTD circuit 400' is an interim modulation technique. Thus, it may be advantageous to simply turn on one or more predetermined resistors, e.g., $R_1$ and $R_2$, since full HV pulse emulation is expected to start approximately 25 µsec after the HV pulse is initiated.

| Range | In Range | Out of Range |
| --- | --- | --- |
| $R_1$ On and $R_2$ On | 11 1x xx xx | 11 0x xx xx |
| $R_1$ On and $R_2$ Off | 11 0x xx xx | 00 1x xx xx |
| $R_1$ Off and $R_2$ On | 00 1x xx xx | 00 0x xx xx |

When the entire output word from A/D converter 420 is available, step 10 is performed to determine whether the RC characteristic is linear. It will be appreciated that the RC characteristic is linear only if the capacitance C to be emulated is linear and the resistance $R_L$ is constant throughout the HV pulse. In an exemplary case, the voltage characteristic of capacitance C is preferably determined when the capacitance value is set during step 6. It will be noted that a minimal implementation of step 10 would be to check for the presence of a flag indicative of a non-linear capacitance voltage characteristic or variable $R_L$, which flags can be set during step 6.

In the event the capacitance C is to emulated as a linear device and $R_L$ is assumed to be constant, variable capacitance emulation using a constant voltage characteristic is performed during step 15. It should be noted that this is "open-loop" control method. However, in the event that the capacitance C to be emulated is non-linear or $R_L$ is variable, the subroutine including steps 11–14 is performed, thus implementing the "closed-loop" control method. Preferably, for each short interval, e.g.,.20 to 100 µsec, during the HV pulse event, the following subroutine advantageously can be used to determine the ideal HV pulse voltage.

First, the actual load resistance $R_L$ is sampled using, in an exemplary case, the shunt resistor $R_S$ and voltage divider $R_{VD}$ during step 11 and then the C index value is determined for the actual high voltage HV during step 12. Then, the next expected voltage component for the ideal HV pulse is calculated using equation (16) during step 13. It should be noted that the calculated voltage component can be provided to an analog comparator, e.g., the analog comparator 410, via a digital-to-analog converter (DAC) 408. Finally, the modulation technique is initiated so as to advantageously match the instantaneous voltage of the actual HV pulse to the output voltage of the ideal HV pulse during step 14. In short, the resistor taps are servoed to match Vnew during step 14.

Referring again to FIG. 9, it should be noted that the dynamic resistance values generated by the resistor taps can be quite broad, depending on which of the resistors $R_1$–$R_4$ are operated and whether the operated ones of these resistor taps are merely turned On or the operated ones of the resistor taps are PWM controlled. For example, as shown in FIG. 12, the resistance range will appreciably vary depending on whether or not resistor $R_1$ is On, i.e., connected in parallel with the other operated ones of the resistor taps, for each one of the different modulation technique combinations. Moreover, for each of the combinations listed in FIG. 12, there will be one point in the resistance range wherein the error or ripple associated with the emulated resistance $R_{ef}$ is a maximum value. Stated another way, ripple advantageously can be minimized by avoiding the points in the combinations producing the maximum ripple values for a selected $R_{ef}$.

Moreover, it should also be mentioned that the value of $R_{ef}$ and the modulation technique combination needed to achieve the minimum possible ripple are a function of the actual capacitance $C_O$, which was determined during calibration. Thus, given a value of $C_O$, the PWM type encoding and its associated $\alpha_1$ can be stored in a LUT, i.e., either the RAM 530 of MCU 500 or LUT 440, for each of the expected values of $V_S$ read by A/D converter 420, as illustrated in FIG. 13. Thus, the voltage drop at shunt resistance $R_S$, which is indicative of the resistance of $R_L$, advantageously can be used as index values for the LUT; the output of the LUT preferably is a digital word identifying the modulation technique to be implemented, as shown in FIG. 12, and a second digital word identifying the count value corresponding to the $\alpha_1$ portion of the period T, as discussed in greater detail above.

It should be noted that the inventive method works for all PWM based resistor emulation circuits and is not limited to the emulation of a variable capacitance via a variable resistor as described above. It should also be mentioned that while some of these concepts are specific to exponentially decaying RC waveforms, other features according to the present invention are generic and have broader applications.

Other modifications and variations to the invention will be apparent to one of ordinary skill in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A circuit for emulating a variable resistor comprising:
    a first branch including a first resistor $R_1$ having a first value and a first switching element; and
    a second branch including a second resistor $R_2$ having a second value and a second switching element,
    wherein said first and second branches are connected in parallel,
    wherein an effective resistance ($R_{ef}$) to be emulated by the circuit using said first and second resistors $R_1$ and $R_2$ satisfies the condition that $R_1 \leq R_{ef} \leq R_2$, and
    wherein $R_{ef}$ satisfies the expression $$R_{ef} = (R_1 * R_2)/((\alpha_2 * R_1) + (\alpha_1 * R_2))$$

where $\alpha_1$ and $\alpha_2$ denote respective percentages of a unit period of time T during which said first and said second switching elements are conducting such that $\alpha_1 + \alpha_2 = 1$ T.

2. The circuit for emulating a variable resistor as recited in claim 1, wherein said first and second switching elements are transistor switches.

3. The circuit for emulating a variable resistor as recited in claim 2, wherein a voltage less than or equal to approximately 1000 Volts is applied across said first and said second branches and wherein said first and second switching elements are insulated gate bipolar transistor (IGBT) switches.

4. A method for producing a predetermined current flow during a unit period of time in a parallel branch network including a first branch having a first resistance $R_1$ and a first switching element and a second branch having a second resistance $R_2$ and a second switching element to which a fixed potential is applied, said method comprising the steps of:
    determining an effective resistance $R_{ef}$ for the parallel branch network corresponding to the fixed potential divided by the predetermined flow; and
    operating said first and said second switching elements so as to satisfy the expression:

$$R_{ef} = (R_1 * R_2)/((\alpha_2 * R_1) + (\alpha_1 * R_2))$$

where $\alpha_1$ and $\alpha_2$ denote respective percentages of the unit period of time T during which said first and said second switching elements are conducting such that $\alpha_1 + \alpha_2 = 1$ T.

5. The method for producing a predetermined flow as recited in claim 4, wherein said predetermined flow is defined in terms of amperes and wherein said fixed potential is defined in terms of volts.

6. A method for emulating an exponentially decaying waveform associated with a desired capacitance C in a resistor-capacitor (RC) circuit including a capacitor $C_O$ having a fixed capacitance different from the desired capacitance C, the RC circuit including a load resistance $R_L$, the capacitor $C_O$ and parallel first and second branches including first and second resistors $R_1$ and $R_2$ and first and second switching elements, respectively, said method comprising the steps of:

(a) determining an effective resistance $R_{eff}$ which, when operated in parallel with the resistance $R_L$ and the actual capacitor $C_0$, produces a decay constant $\tau$ substantially the same as identical to that produced using only the desired capacitor C and the resistor $R_L$; and (b) when said capacitor $C_0$ is being discharged, operating the first and the second switching elements according to the expression:

$$R_{eff} = (R_1 * R_2)/((\alpha_2 * R_1) + (\alpha_1 * R_2))$$

where $\alpha_1$ and $\alpha_2$ denote respective percentages of a unit period of time T during which the first and the second switching elements are conducting such that $\alpha_1 + \alpha_2 = 1$ T so as to simulate the effective resistance $R_{eff}$ and thereby generate the exponentially decaying waveform.

7. The method for emulating an exponentially decaying waveform as recited in claim 6, wherein said step (a) comprises the steps of:

(a)(i) obtaining a capacitance index table denoting a plurality of capacitance values $C_i$ at a plurality of voltage values $V_i$, respectively;

(a)(ii) generating a decay factor table relating the resistance $R_L$ to the effective resistance $R_{eff}$ for the desired capacitance C such that, for each predetermined time slice during the period T, the expression $V_i = V_{i-1} * e^{-n/\tau}$ is satisfied; and wherein said step (b) comprises the repetitive steps of:

(b)(i) determining a voltage $V_i$ corresponding to the predetermined time slice, respectively; and (b)(ii) operating the first and the second switching elements during each time slice of the period T according to the expression:

$$R_{eff} = (R_1 * R_2)/((\alpha_2 * R_1) + (\alpha_1 * R_2))$$

where $\alpha_1$ and $\alpha_2$ denote respective percentages of a unit period of time T during which the first and the second switching elements are conducting such that $\alpha_1 + \alpha_2 = 1$ T so as to simulate the effective resistance $R_{eff}$ and thereby generate the exponentially decaying waveform having a profile corresponding to the capacitance index table.

8. The method for emulating an exponentially decaying waveform as recited in claim 7, wherein said capacitance index table defines a non-linear capacitor.

9. The method for emulating an exponentially decaying waveform as recited in claim 6, wherein said step (a) comprises the steps of:

(a)(i) obtaining a capacitance index table denoting a plurality of capacitance values $C_i$ at a plurality of voltage values $V_i$, respectively;

(a)(ii) generating a decay factor table relating substantially all possible values of the resistance $R_L$ to the effective resistance $R_{eff}$ for the desired capacitance C such that, for each predetermined time slice during the period T, the expression $V_i = V_{i-1} * e^{-n/\tau}$ is satisfied; and (a)(iii) determining an actual resistance $R_L$, and wherein said step (b) comprises the repetitive steps of:

(b)(i) determining a voltage $V_i$ corresponding to the predetermined time slice, respectively, for said actual resistance $R_L$; and (b)(ii) operating the first and the second switching elements during each time slice of the period T according to the expression:

$$R_{eff} = (R_1 * R_2)/((\alpha_2 * R_1) + (\alpha_1 * R_2))$$

where $\alpha_1$ and $\alpha_2$ denote respective percentages of a unit period of time T during which the first and the second switching elements are conducting such that $\alpha_1 + \alpha_2 = 1$ T so as to simulate the effective resistance $R_{eff}$ and thereby generate the exponentially decaying waveform having a profile corresponding to the capacitance index table.

10. The method for emulating an exponentially decaying waveform as recited in claim 9, wherein said capacitance index table defines a non-linear capacitor.

11. An emulation circuit for emulating a variable resistor comprising:

a first branch including a first resistor $R_1$ having a first value and a first switching element $S_1$;

a second branch including a second resistor $R_2$ having a second value and a second switching element $S_2$;

a third branch including a third resistor $R_3$ having a third value and a third switching element $S_3$;

a fourth branch including a fourth resistor $R_4$ having a fourth value and a fourth switching element $S_4$; and a driver circuit, operatively connected to said switching elements $S_1, S_2, S_3$ and $S_4$, generating at least one pulse width modulation control signal;

wherein said first, said second, said third and said fourth branches are all connected to one another in parallel, wherein $R_1 < R_2 < R_3 < R_4$, and wherein at least one of said switching elements $S_1, S_2, S_3$ and $S_4$ is turned On and Off responsive to said at least one PWM control signal corresponding to a duty cycle of a corresponding one of said $R_1, R_2, R_3$ and $R_4$ resistors with a range of about 10% to 90%.

12. The emulation circuit as recited in claim 11, wherein, for an emulated resistance value, said at least one PWM control signal comprises first and second PWM control signals, wherein first and second selected ones of said switching elements $S_1, S_2, S_3$ and $S_4$ are provided with respective first and second PWM control signals so as to emulate an effective resistance $R_{eff}$ using respective first and second selected resistors $R_{S1}$ and $R_{S2}$, and wherein said resistance $R_{eff}$ satisfies the expression $$R_{eff} = (R_{S1} * R_{S2})/((\alpha_2 * R_{S1}) + (\alpha_1 * R_{S2}))$$

where $\alpha_1$ and $\alpha_2$ denote respective percentages of a unit period of time T during which said first and said second selected ones of said switching elements $S_1, S_2, S_3$ and $S_4$ are conducting such that $\alpha_1 + \alpha_2 = 1$ T.

13. The emulation circuit as recited in claim 12, wherein said switching elements $S_1, S_2, S_3$ and $S_4$ are transistor switches.

14. The emulation circuit as recited in claim 13, wherein a voltage less than or equal to approximately 1000 Volts is applied across all of said branches and wherein switching elements $S_1, S_2, S_3$ and $S_4$ are insulated gate bipolar transistor (IGBT) switches.

15. The emulation circuit as recited in claim 12, wherein a third selected one of said switching elements $S_1, S_2, S_3$ and $S_4$ is continuously energized so as to bias said emulation circuit.

16. The emulation circuit as recited in claim 11, wherein an emulated resistance value comprises an emulated resistance range including first and second subranges, wherein said at least one PWM control signal comprises first, second and third PWM control signals, wherein first selected ones of said first, said second and said third switching elements $S_1$, $S_2$, and $S_3$ are provided with selected ones of said first, said second and said third PWM control signals so as to emulate an effective resistance $R_{eff}$ within said first subrange, wherein second selected ones of said first, said second and said third switching elements $S_1$, $S_2$, and $S_3$ are provided with selected ones of said first, said second and said third PWM control signals so as to emulate an effective resistance $R_{eff}$ within said second subrange, wherein said effective resistance $R_{eff}$ satisfies the expression $$R_{eff} = (R_{S1} * R_{S2})/((\alpha_2 * R_{S1}) + (\alpha_1 * R_{S2}))$$

where $\alpha_1$ and $\alpha_2$ denote respective percentages of a unit period of time T during which said first and said second selected ones of said switching elements $S_1$, $S_2$, $S_3$ and $S_4$ are conducting such that $\alpha_1 + \alpha_2 = 1$ T, where first and second selected resistances $R_{S1}$ and $R_{S2}$ denote respective ones of said resistors energized by said first and said second selected ones of said switching elements $S_1$, $S_2$, and $S_3$, and wherein said first and said second selected ones of said switching element $S_1$, $S_2$ and $S_3$ define disjoint sets of said switching element $S_1$, $S_2$ and $S_3$.

17. The emulation circuit as recited in claim 16, wherein said switching elements $S_1$, $S_2$, $S_3$ and $S_4$ are transistor switches.

18. The emulation circuit as recited in claim 17, wherein a voltage less than or equal to approximately 1000 Volts is applied across all of said branches and wherein switching elements $S_1$, $S_2$, $S_3$ and $S_4$ are insulated gate bipolar transistor (IGBT) switches.

19. The emulation circuit as recited in claim 16, wherein, for said emulated resistance value, a fourth selected one of said switching elements $S_1$, $S_2$, $S_3$ and $S_4$ is continuously energized by a constant voltage so as to bias said emulation circuit.

* * * * *